(12) United States Patent
Yamagata

(10) Patent No.: US 11,492,585 B2
(45) Date of Patent: Nov. 8, 2022

(54) CELL IDENTIFICATION SYSTEM AND CELL IDENTIFICATION METHOD

(71) Applicant: Canon Medical Systems Corporation, Otawara (JP)

(72) Inventor: Hitoshi Yamagata, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 104 days.

(21) Appl. No.: 16/885,448

(22) Filed: May 28, 2020

(65) Prior Publication Data

US 2020/0377842 A1 Dec. 3, 2020

(30) Foreign Application Priority Data

May 31, 2019 (JP) .............................. JP2019-102826
May 26, 2020 (JP) .............................. JP2020-091303

(51) Int. Cl.
- *G06K 9/00* (2022.01)
- *C12M 1/34* (2006.01)
- *G06T 7/00* (2017.01)

(52) U.S. Cl.
CPC ............ *C12M 41/36* (2013.01); *G06T 7/0016* (2013.01); *G06T 2200/24* (2013.01); *G06T 2207/10016* (2013.01); *G06T 2207/30024* (2013.01); *G06T 2207/30242* (2013.01)

(58) Field of Classification Search
CPC ..................................................... C12M 41/36
See application file for complete search history.

(56) References Cited

U.S. PATENT DOCUMENTS

| | | | |
|---|---|---|---|
| 2015/0232907 A1* | 8/2015 | Wang ................. | G01N 35/1011 506/39 |
| 2018/0011084 A1* | 1/2018 | Fois ...................... | G01N 21/255 |
| 2018/0045641 A1* | 2/2018 | Zeder ..................... | B01L 3/5085 |

(Continued)

FOREIGN PATENT DOCUMENTS

| | | | | |
|---|---|---|---|---|
| WO | WO 01/35071 A2 | 5/2001 | | |
| WO | WO-2012176114 A1 * | 12/2012 | ............ | A61B 5/1128 |
| WO | WO-2018223142 A1 * | 12/2018 | ............. | C12M 41/36 |

OTHER PUBLICATIONS

Christiansen, E. M., et al., "In Silico Labeling: Predicting Fluorescent Labels in Unlabeled Images," Cell, vol. 173, Apr. 19, 2018, 12 pages.

(Continued)

*Primary Examiner* — Oneal R Mistry
(74) *Attorney, Agent, or Firm* — Oblon, McClelland, Maier & Neustadt, L.L.P.

(57) ABSTRACT

According to one embodiment, a cell identification system includes an imaging device and an identification device. The imaging device includes a well plate, a rotation mechanism, and an imaging part. The well plate is provided with a plurality of wells capable of accommodating cells. The rotation mechanism rotates the cells. The imaging part images the cells. The identification device includes processing circuitry. The processing circuitry controls the rotation mechanism to rotate the cells, controls the imaging part to image the cells each time the cells are rotated by the rotation mechanism, and inputs an image for the cells captured by the imaging part to a learned model so as to identify a cell in a good state from among the cells.

13 Claims, 17 Drawing Sheets

(56) References Cited

U.S. PATENT DOCUMENTS

| | | | | |
|---|---|---|---|---|
| 2018/0292397 A1* | 10/2018 | Nguyen | ............... | G01N 35/028 |
| 2019/0120831 A1* | 4/2019 | Li | .................... | G01N 33/54393 |
| 2019/0344265 A1* | 11/2019 | Qin | .................. | B01L 3/502715 |
| 2020/0017823 A1* | 1/2020 | Murphy | ............... | C12N 5/0619 |
| 2020/0131465 A1* | 4/2020 | Floto | .................... | G06K 9/2081 |
| 2020/0401785 A1* | 12/2020 | Woehler | ............. | G01N 21/6428 |

OTHER PUBLICATIONS

"[Shimadzu] Birth of a new cell process management system Release of "Culturescanner CS-1" cell culture analyzer," Tokio X'Press, Sep. 2017, http://www.shimadzu.co.jp/news/press/n00kbc000000dmzs.html, 2 pages.

"Cell culture analyzer Culture Scanner CS-1,", Shimadzu, Jul. 2019, https://www.an.shimadzu.co.jp/bio/cell/cs1/index/htm, (with English Translation), 4 pages.

\* cited by examiner

CELL IDENTIFICATION SYSTEM AND CELL IDENTIFICATION METHOD

CROSS-REFERENCE TO RELATED APPLICATIONS

This application is based upon and claims the benefit of priority from Japanese Patent Application No. 2019-102826, filed May 31, 2019; and No. 2020-91303, filed May 26, 2020; the entire contents of both of which are incorporated herein by reference.

FIELD

Embodiments described herein relate generally to a cell identification system and a cell identification method.

BACKGROUND

Regenerative medical treatments using pluripotent stem cells, such as iPS cells, have already been brought into use clinically. An iPS cell is established via the provision of a reprogramming inducing factor to a differentiated somatic cell. However, the success rate of generating cells usable as iPS cells is low, and the success rate of achieving a usable cell formation from among cells formed post-reprogramming inducing factor introduction is about 10%.

Thus, in an iPS cell establishment culturing process, an operation for sorting good iPS cells is required. In general, a researcher skilled in identification observes cells one by one so as to identify and sort cells in a good state. However, cell sorting by a person has placed a significant burden on researchers and is one of the factors responsible for the high costs of iPS cell generation.

DETAILED DESCRIPTION

In general, according to one embodiment, a cell identification system includes an imaging device and an identification device. The imaging device includes a well plate, a rotation mechanism, and an imaging part. The well plate is provided with a plurality of wells capable of accommodating cells. The rotation mechanism rotates the cells accommodated in the wells. The imaging part images the cells accommodated in the wells. The identification device includes processing circuitry. The processing circuitry controls the rotation mechanism to rotate the cells accommodated in the wells, controls the imaging part to image the cells accommodated in the wells each time the cells are rotated by the rotation mechanism, and inputs an image for the cells accommodated in the wells captured by the imaging part to a learned model so as to identify a cell in a good state from among the cells accommodated in the wells.

Hereinafter, embodiments will be described with reference to the accompanying drawings. Note that the following embodiments will assume, by way of example, instances of iPS cells. However, applicable cells are not limited to iPS cells. The embodiments may discretionarily be applied to cells other than iPS cells. In addition, the following embodiments are preferable in a case where cells are substantially spherical in shape.

First Embodiment

Figure 1:
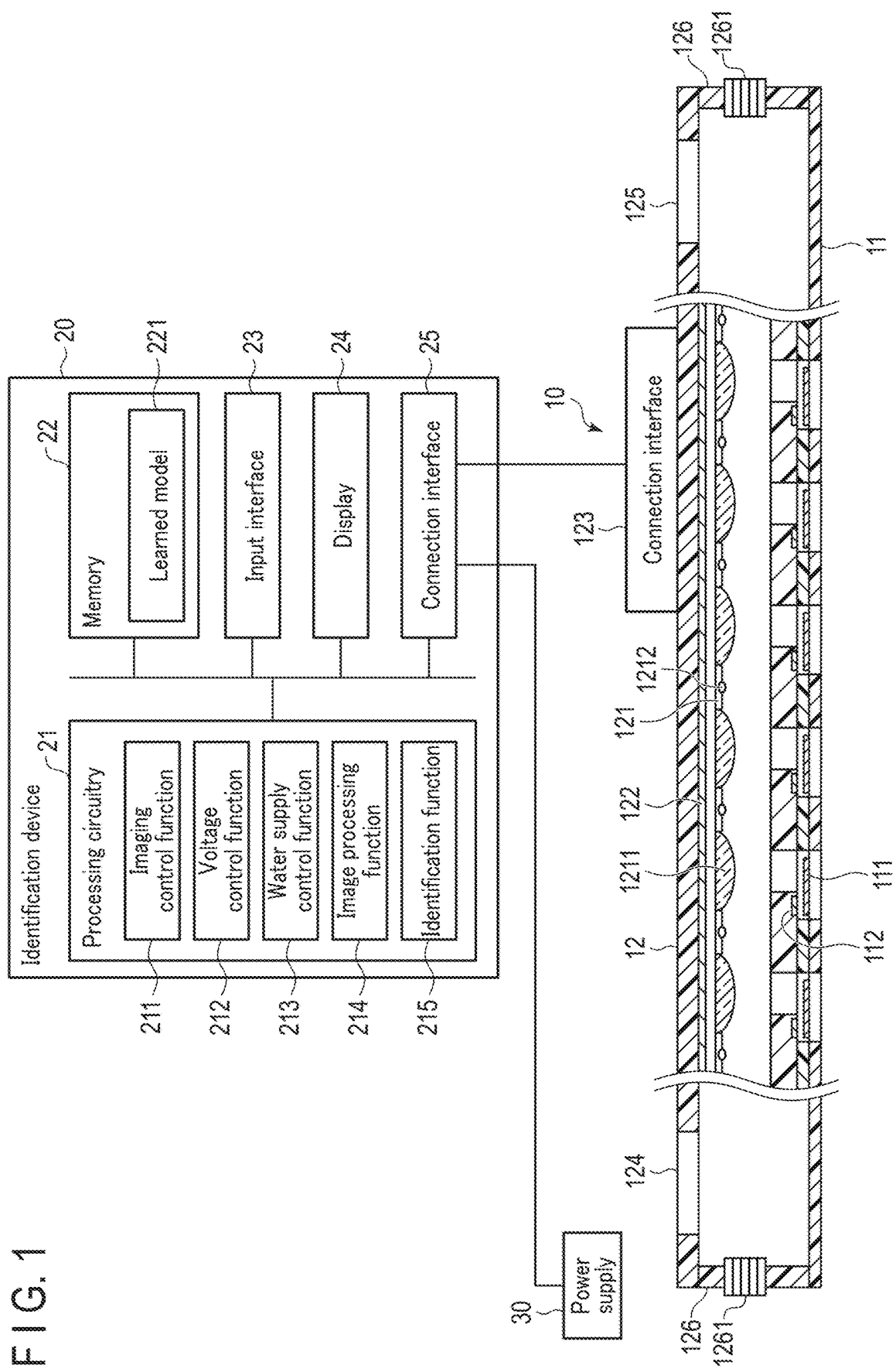
FIG. 1 is a diagram showing a configuration of a cell identification system according to a first embodiment.

FIG. 1 is a diagram showing an example of a configuration of a cell identification system according to a first embodiment. The cell identification system shown in FIG. 1 includes an imaging device 10 and an identification device 20. FIG. 1 shows a schematic diagram of a cross section of the imaging device 10 and a block diagram of the identification device 20. The imaging device 10 and the identification device 20 are, for example, wire-connected. In addition, the identification device 20 is connected to a power supply 30 that applies a voltage to the imaging device 10.

The imaging device 10 is a device capable of accommodating iPS cells and imaging the accommodated iPS cells. The imaging device 10 includes a well plate 11 for accommodating the iPS cells, and a lid part 12 that tightly covers the well plate 11.

Figure 2:
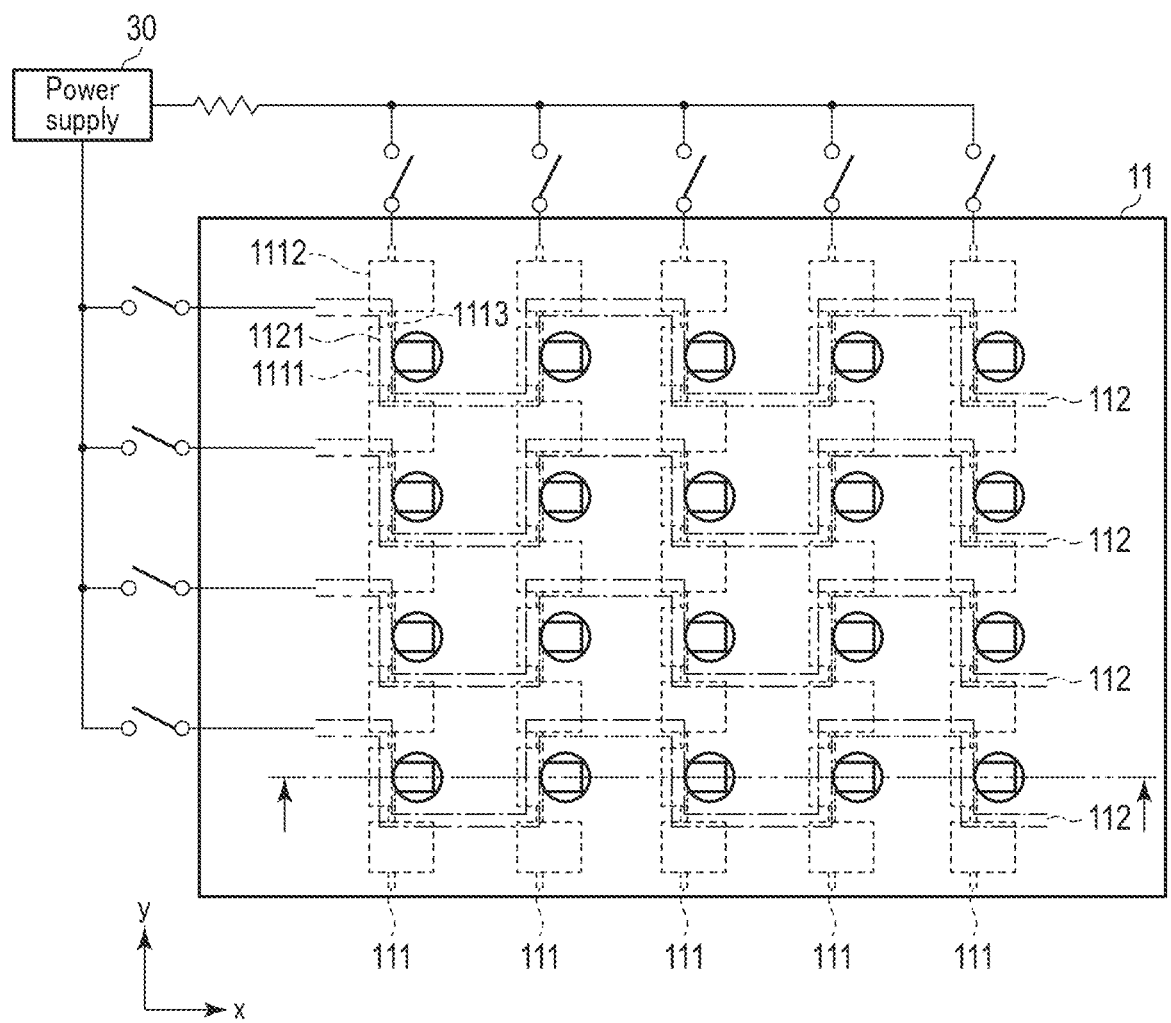
FIG. 2 is a diagram showing a top view of a well plate shown in FIG. 1.

FIG. 2 shows an example of a top view of the well plate 11 according to the first embodiment. The cross-sectional diagram shown in FIG. 1 shows a cross section of the well plate 11 taken along a two-dot chain line shown in FIG. 2. In the well plate 11, a plurality of recesses called wells are formed, for example, in a lattice pattern on its top surface. In other words, a well array is formed on the well plate 11. Each of the wells is formed into a cylindrical shape having an approximately circular cross section. The diameter of each well is about 15 μm to 20 μm, and is larger than the diameter of an iPS cell.

The well plate 11 is produced using, for example, PDMS (polydimethylsiloxane) or Si. Inside the well plate 11, rotation mechanisms that rotate iPS cells selectively accommodated in the respective wells are formed. The rotation mechanisms are realized by, for example, a first electrode 111 and a second electrode 112 formed inside the well plate 11. By the first electrode 111 and the second electrode 112, for example, an electrostatic drive type torsional vibrator as a rotational actuator is formed in each well.

Specifically, the first electrode 111 and the second electrode 112 are respectively formed in preset directions. For example, in an example shown in FIG. 2, the first electrodes 111 are indicated by broken lines and formed along a y-axis direction. In addition, the second electrodes 112 are indicated by one-dot chain lines and formed along an x-axis direction.

Each of the first electrodes 111 includes a movable electrode plate 1111, a fixing part 1112, and a torsion bar 1113. The movable electrode plate 1111 is formed in each well to take the form of a partition plate of the cylindrical structure inside the well. The movable electrode plate 1111 functions as a bottom portion of each well. The movable electrode plate 1111 is supported by the fixing part 1112 fixed by an insulating layer via the torsion bar 1113. The periphery of the movable electrode plate 1111 is formed with a space so that the movable electrode plate 1111 is rotatable around the torsion bar 1113.

The second electrode 112 includes a fixed electrode part 1121. The fixed electrode part 1121 is provided at a position facing the movable electrode plate 1111. The second electrode 112 is formed in a layer above the first electrode 111 so that the fixed electrode part 1121 attracts the movable electrode plate 1111 in a vertically upward direction.

Courtesy of the movable electrode plate 1111, the fixing part 1112, the torsion bar 1113, and the fixed electrode part 1121, an electrostatic drive type torsional vibrator is formed in each well.

Between the first electrodes 111 and the second electrodes 112, the power supply 30 is connected via switches. When switches of the first electrode 111 formed in a predetermined column and the second electrode 112 formed in a predetermined row are turned on, a voltage is applied between the movable electrode plate 1111 and the fixed electrode part 1121 specified by this row and column. Thereby, electrostatic attraction is generated between the movable electrode plate 1111 and the fixed electrode part 1121, and the movable electrode plate 1111 rotates around the torsion bar 1113.

The rotation mechanism is not limited to an electrostatic drive type torsional vibrator formed by the first electrode 111 and the second electrode 112. For example, the rotation mechanism may be other actuators.

The lid part 12 shown in FIG. 1 is produced using, for example, PDMS or Si. At a part of an upper internal surface of the lid part 12, an imaging part for imaging the iPS cells accommodated in the wells of the well plate 11 is provided. The imaging part includes, for example, a plurality of minute lens elements 1211 and an image sensor 122. In the following, it is assumed that a plurality of wells are formed in a lattice pattern on the well plate 11, and a microlens array 121 formed of a plurality of lens elements 1211 arranged in a lattice pattern in the same manner as the wells is assumed.

The microlens array 121 is an example of an optical system for forming an image of an imaging object on a light-receiving surface of the image sensor 122. In the microlens array 121, the plurality of minute lens elements 1211 are arranged on a substrate, for example. The arrangement of the lens elements 1211 is coincident with that of the wells formed in the well plate 11.

Light sources 1212 are provided in the microlens array 121. Each of the light sources 1212 is realized by, for example, a white LED capable of broadband measurement, or an LED having a specific wavelength, etc. Each of the light sources 1212 is provided, for example, between adjacent lens elements 1211 as shown in FIG. 1. From the light sources 1212, light having energy of a degree not liable to damage the iPS cells accommodated in the wells is emitted. An installation location of the light sources 1212 is not limited thereto. In a case where the well plate 11 is formed by, for example, PDMS, the light sources 1212 may be provided at a position facing the lens element 1211 with the wells therebetween.

The image sensor 122 is an example of an image sensor that converts the received light into an electric signal. The image sensor 122 is realized by, for example, a CCD sensor or a CMOS sensor. The image sensor 122 receives light emitted from the light sources 1212 and reflected and scattered by the imaging object through the microlens array 121. The image sensor 122 converts the received light into an image signal as an electric signal.

On an upper external surface of the lid part 12, for example, a connection interface 123 for connecting the imaging part and the identification device 20 is provided. The connection interface 123 includes, for example, a connection terminal, and is connected with the identification device 20 via the connection terminal so as to receive a control signal from the identification device 20 and transmit the image signal output from the image sensor 122 to the identification device 20.

On an upper surface of an area where the imaging part is not provided at an end of the lid part 12, a first hole 124 is provided. In addition, on an upper surface of an area where the imaging part is not provided at the other end of the lid part 12, a second hole 125 is provided. The first hole 124 is used as, for example, an inflow port that allows a solution such as a buffer solution to flow into the imaging device 10. In addition, the second hole 125 is used as, for example, a discharge port that discharges a solution such as a buffer solution from the imaging device 10. As a buffer solution, for example, phosphate buffered salts (PBS) is used. The diameter of each of the first hole 124 and the second hole 125 is, for example, larger than that of an iPS cell.

The lid part 12 includes a side wall part 126. On at least a part of the side wall part 126, for example, an extendable part 1261 capable of extending and contracting in an extending direction of the side wall part 126 is formed. The extendable part 1261 is an example of a distance adjustment mechanism. The extendable part 1261 is realized by, for example, a bellows structure, a nesting structure, etc. By the extension and contraction of the extendable part 1261, a distance between the top surface of the well plate 11 and the microlens array 121 changes.

The well plate 11 and the lid part 12 are aligned so that the position of the plurality of wells formed in the well plate 11 and that of the microlens array 121 provided in the lid part 12 are matched. When the alignment of the well plate 11 and the lid part 12 is completed, a lower end portion of the side wall part 126 of the lid part 12 is joined to the well plate 11 to produce the imaging device 10. The height from an undersurface of the well plate 11 to a top surface of the lid part 12 is, for example, about 2 mm.

The identification device 20 shown in FIG. 1 is a device that identifies iPS cells in a good state from among the iPS cells accommodated in the imaging device 10 by using a learned model. The identification device 20 includes processing circuitry 21, a memory 22, an input interface 23, a display 24, and a connection interface 25. The processing circuitry 21, the memory 22, the input interface 23, the display 24, and the connection interface 25 are, for example, communicatively connected to one another via a bus.

The processing circuitry 21 is a processor functioning as a main device of the identification device 20. The processing circuitry 21 executes a program stored in the memory 22, etc. so as to realize a function corresponding to the program.

The memory 22 is a storage device, such as a read only memory (ROM), a random access memory (RAM), a hard disk drive (HDD), a solid state drive (SSD), an integrated circuit storage device, etc., which stores various types of information. The memory 22 may be, for example, a drive that reads and writes various kinds of information from and in a portable storage medium such as a CD-ROM drive, a DVD drive, or a flash memory, etc. The memory 22 need not necessarily be realized by a single storage device. The memory 22 may be realized by, for example, a plurality of storage devices. Also, the memory 22 may be arranged in another computer connected to the identification device 20 via a network.

The memory 22 stores an identification program, etc. according to the present embodiment. These programs may be, for example, stored in the memory 22 in advance. Also, these programs may be stored in a non-transitory storage medium and distributed, read from the non-transitory storage medium, and installed in the memory 22.

The memory 22 stores, for example, a learned model 221 as an identifier generated by machine learning. The learned model 221 may be stored in the memory 22 at any point in time after the identification device 20 is manufactured. For example, the storing may be performed at a given point in time between the manufacture and installation to a medical facility, etc., or at a time of maintenance.

The learned model 221 can be obtained by performing machine learning on a machine learning model in accordance with a model learning program based on learning data. In the present embodiment, the learned model 221 is, for example, provided with a function to evaluate a state of an iPS cell based on an input of an image. In this case, the learning data includes, for example, input data, which is an image obtained by imaging an iPS cell, and correct answer output data indicating whether the state of the iPS cell within the image is good or bad.

Figure 3:
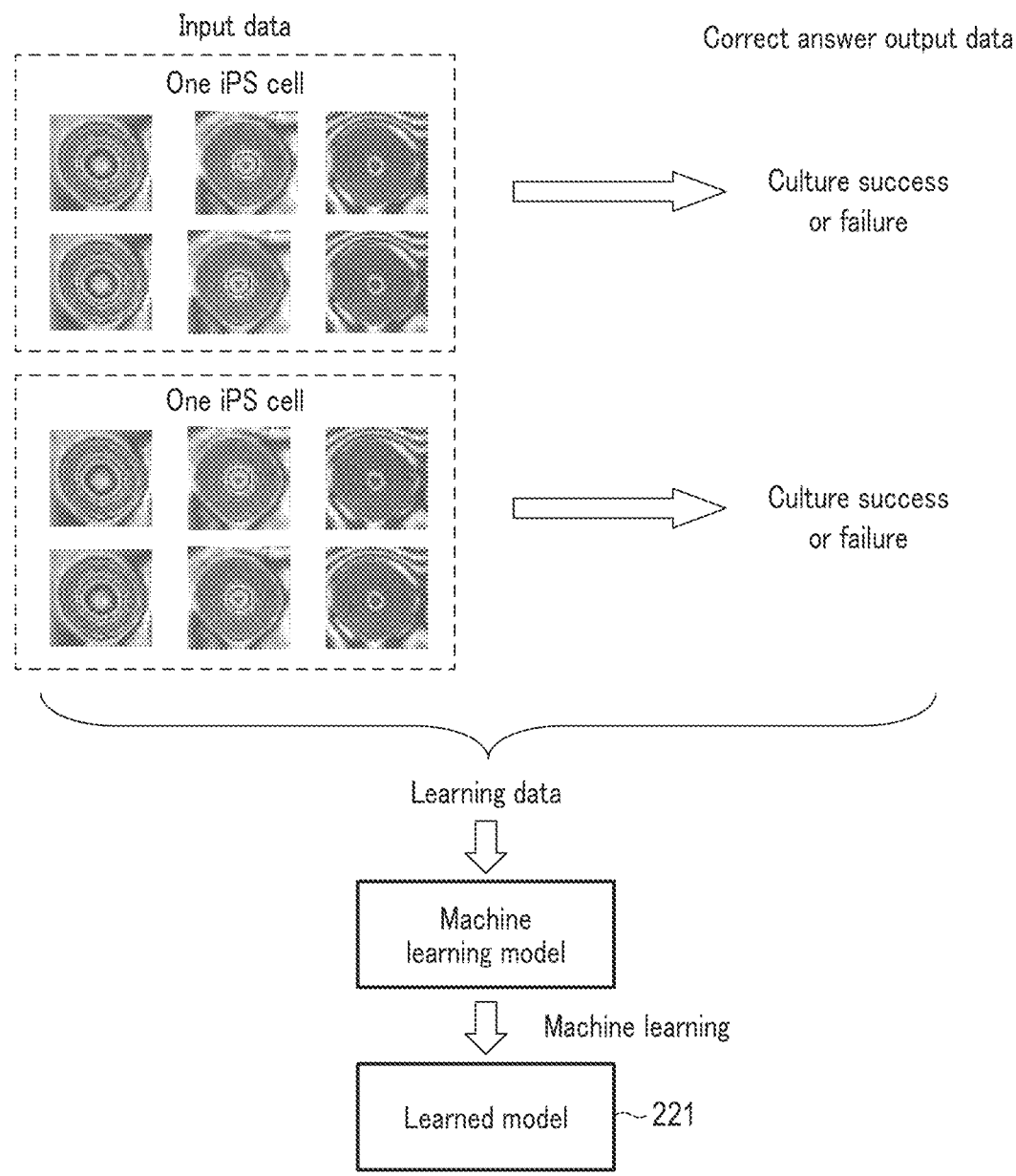
FIG. 3 is a diagram for explaining processing when a learned model shown in FIG. 1 is generated.

FIG. 3 is a diagram for explaining an example of processing when the learned model 221 shown in FIG. 1 is generated based on the learning data. The input data is, for example, a plurality of images obtained by imaging a plurality of iPS cells one by one. At this time, for each iPS cell, a plurality of images are used as the input data. For example, images capturing one iPS cell from multiple angles by rotating the iPS cell using the rotation mechanism and images obtained by capturing one iPS cell while changing a distance between the iPS cell and the lens, are used as the input data. Then, for example, whether or not the iPS cell with these plural images obtained has been successfully cultured as a good cell is set as the correct answer output data. Using the image obtained by imaging while changing the distance between the iPS cell and the lens as the input data renders it possible to generate a model in which an interference pattern of light passing through the iPS cell is also taken into consideration.

The machine learning model according to the present embodiment is, for example, a composite function with parameters obtained by combining a plurality of functions. A composite function with parameters is defined by a combination of a plurality of adjustable functions and parameters. The machine learning model according to the present embodiment may be any composite function with parameters satisfying the above-described requirements, and is assumed to be a multilayer network model (hereinafter, referred to as a "multi-layered network"). The learned model 221 using the multi-layered network includes an input layer to input an image, an output layer to output whether the state of the iPS cell is good or bad, and at least one intermediate layer or hidden layer provided between the input layer and the output layer. The learned model 221 is assumed to be used as a program module that is a part of artificial intelligence software.

As the multi-layered network according to the present embodiment, for example, a deep neural network (DNN), which is a multilayer neural network to be the target of deep learning, is used. As the DNN, for example, a convolution neural network (CNN) targeting an image may be used.

The input interface 23 shown in FIG. 1 receives various types of input operations from the user, converts a received input operation into an electric signal, and outputs the electric signal to the processing circuitry 21. The input interface 23 is connected to, for example, an input device such as a mouse, a keyboard, a trackball, a switch, a button, a joystick, a touch pad, and a touch panel to which an instruction is input by a touch on its operation surface. The input device connected to the input interface 23 may be an input device provided on another computer connected via a network, etc.

The display 24 displays various types of information in accordance with an instruction from the processing circuitry 21. As the display, any display, such as a cathode ray tube (CRT) display, a liquid crystal display, an organic EL display, an LED display, or a plasma display, can be used as appropriate.

The connection interface 25 is an interface between the identification device 20 and the other devices. Specifically, the connection interface 25 is connected to, for example, the connection interface 123 of the imaging device 10, the power supply 30, a pump (not shown), etc. The connection interface 25 includes an analog-to-digital converter, converts an image signal output from the connection interface 123 into digital format image data, and outputs the image data to the processing circuitry 21 of the identification device 20. The connection interface 25 also outputs a control signal generated at the processing circuitry 21 to the power supply 30 and the pump.

The processing circuitry 21 executes the identification program, etc. stored in the memory 22 so as to realize a function corresponding to the program. For example, through execution of the identification programs, the processing circuitry 21 performs an imaging control function 211, a voltage control function 212, a water supply control function 213, an image processing function 214, and an identification function 215. In the present embodiment, a case where the imaging control function 211, the voltage control function 212, the water supply control function 213, the image processing function 214, and the identification function 215 are realized by a single processor is described; however, the present invention is not limited thereto. For example, a plurality of independent processors may be combined to form processing circuitry so that each of the processors executes the program to thereby realize the imaging control function 211, the voltage control function 212, the water supply control function 213, the image processing function 214, and the identification function 215.

The imaging control function 211 is a function to control the imaging part provided in the imaging device 10, and is an example of an imaging control part.

The voltage control function 212 is a function to control application of a voltage to the electrodes arranged in the well plate 11. Through application of a voltage to the electrodes, the rotation mechanism provided in each well is driven to rotate the iPS cell accommodated in the well. Thus, the voltage control function 212 can be said to be, in other words, a rotation control function (rotation controller) to control rotation of the iPS cells accommodated in the wells.

The water supply control function 213 is a function to control the pump (not shown) to thereby supply a solution such as a buffer solution to the imaging device 10. By supplying the solution such as a buffer solution into the imaging device 10, the buffer solution flows over the wells, and the iPS cells accommodated in the wells are rotated. Thus, the water supply control function 213 can be said, in other words, to be a rotation control function to control rotation of the iPS cells accommodated in the wells.

The image processing function 214 is a function for generating an image by performing predetermined image processing on image data.

The identification function 215 is a function for identifying iPS cells in a good state by using the learned model 221 with the generated image as an input, and is an example of an identification part.

Next, the identification processing of iPS cells by the identification device 20 configured as described above will be described in accordance with a processing procedure of the processing circuitry 21.

Figure 4:
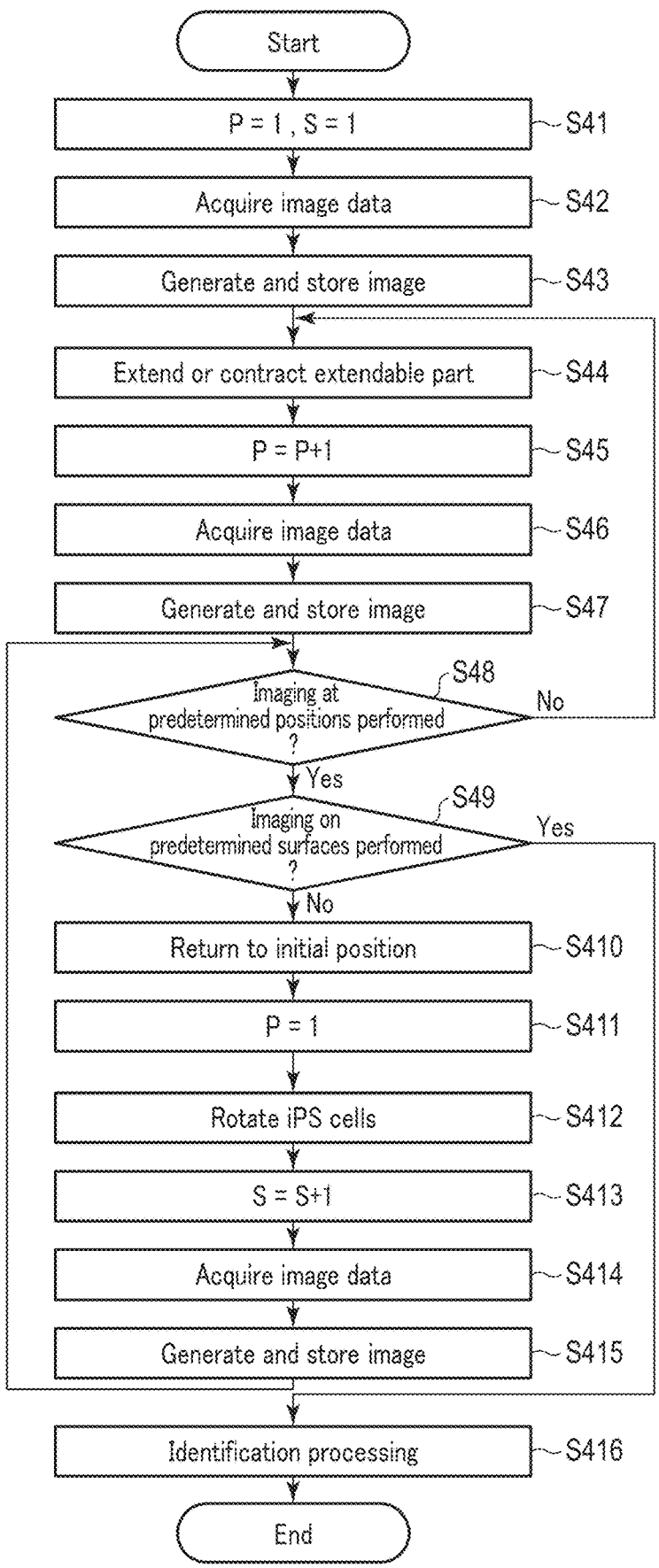
FIG. 4 is a flowchart showing operations performed when processing circuitry shown in FIG. 1 executes identification processing.
Figure 5:
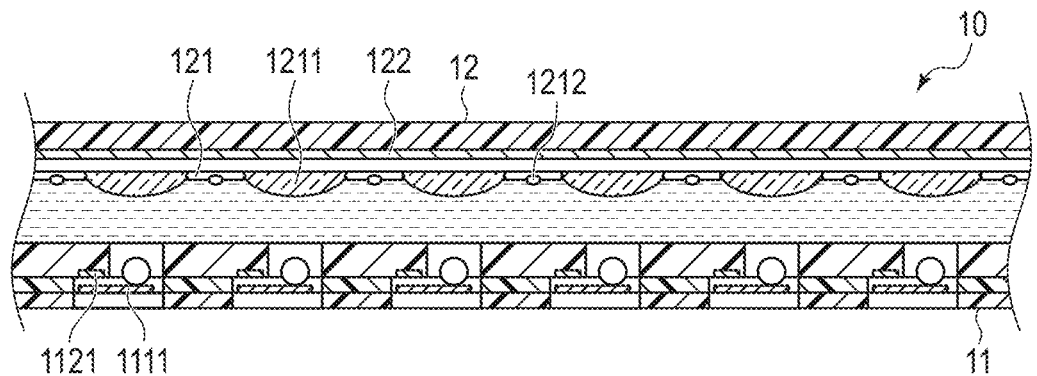
FIG. 5 is a cross-sectional diagram of an imaging device accommodating iPS cells.

FIG. 4 is a flowchart showing an example of operations performed when the processing circuitry 21 shown in FIG. 1 executes identification processing of iPS cells using the learned model 221. In the explanation of FIG. 4, a case where the iPS cells are accommodated in the wells inside the imaging device 10 as shown in FIG. 5 will be described as an example. A timing to execute the identification processing of the iPS cells may be before or after differentiation of the iPS cells. As shown in FIG. 5, each iPS cell is placed on the movable electrode plate 1111 in the well as a bottom portion. The imaging device 10 is filled with, for example, a buffer solution, etc.

First, when an operator of the identification device 20 inputs an instruction to start identification processing to the identification device 20 via the input interface 23, the processing circuitry 21 of the identification device 20 reads an identification program from the memory 22 and executes the read identification program. When the processing circuitry 21 executes the identification program, processing shown in FIG. 4 is started.

In FIG. 4, the processing circuitry 21 executes the imaging control function 211. When the imaging control function 211 is executed, the processing circuitry 21 sets a first position: P=1 of the microlens array 121 with respect to the well plate 11 and a first surface: S=1 of the iPS cells accommodated in the wells (step S41). When (P=1, S=1) is set, the processing circuitry 21 acquires image data for the iPS cells (step S42).

Figure 6:
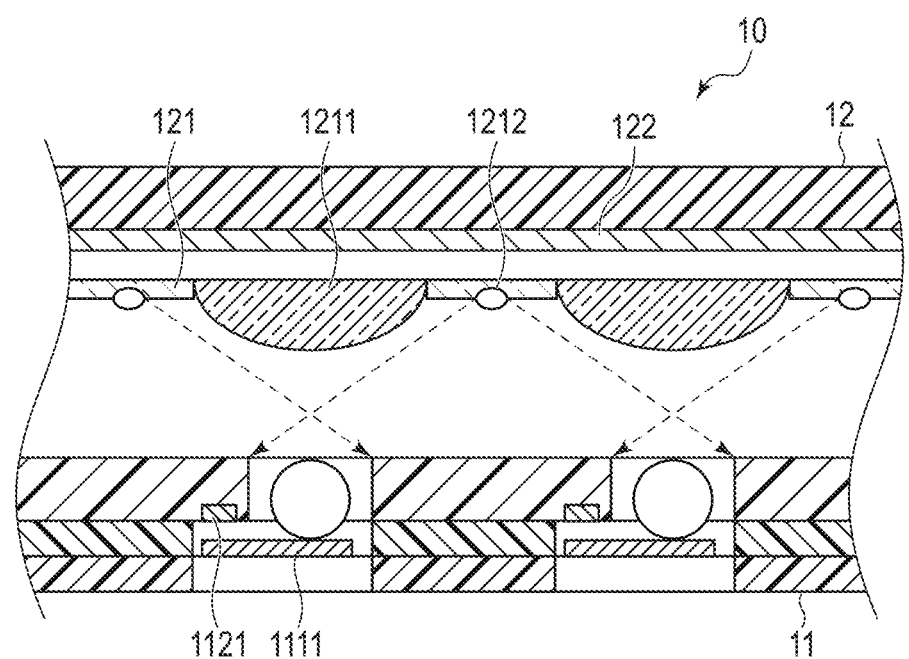
FIG. 6 is a diagram showing a state in which a light source is turned on inside the imaging device shown in FIG. 5.

Specifically, the image data for the iPS cells is acquired in the following manner, for example. The processing circuitry 21 turns on the light sources 1212. FIG. 6 is a diagram showing an example of a case where the light sources 1212 are turned on inside the imaging device 10 shown in FIG. 5. White light generated by the light sources 1212 is applied to the iPS cells accommodated in the wells. The applied light is reflected and scattered by surfaces and internal particles of the iPS cells, and reaches the image sensor 122 via the microlens array 121. The image sensor 122 converts the received light into an electric signal. The electric signal converted by the image sensor 122 is transmitted to the identification device 20 as an image signal via the connection interface 123. The image signal is converted into image data by the connection interface 25 of the identification device 20, and output to the processing circuitry 21.

When the image data is received, the processing circuitry 21 executes the image processing function 214. When the image processing function 214 is executed, the processing circuitry 21 performs predetermined image processing on the received image data to generate an image. The processing circuitry 21 stores the generated image in the memory 22 (step S43).

Figure 7:
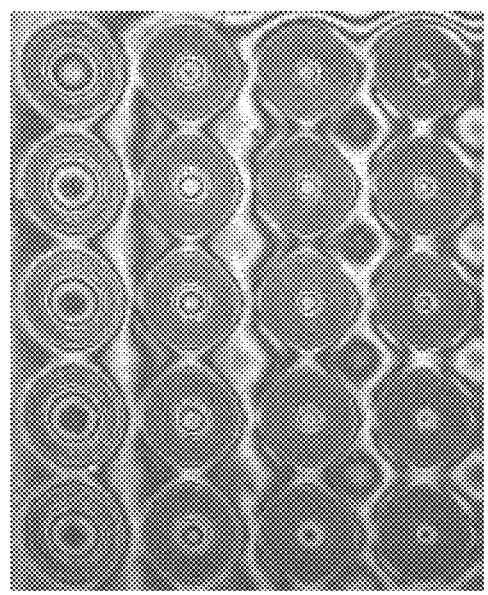
FIG. 7 is a diagram showing an image generated by image processing of the processing circuitry according to the first embodiment.

FIG. 7 is a diagram showing an example of an image generated by the image processing of the processing circuitry 21 according to the first embodiment. As shown in FIG. 7, the iPS cells respectively accommodated in a plurality of wells are included in the image.

When the image is stored in the memory 22, the processing circuitry 21 causes the extendable part 1261, which is a distance adjustment mechanism, to extend or contract by the imaging control function 211 (step S44). Through this process, the microlens array 121 is moved to a second position: P=2. The processing circuitry 21 may cause the extendable part 1261 to, for example, extend or contract for only a preset distance. When the extendable part 1261 is caused to extend or contract, the processing circuitry 21 increments the set position number (step S45). Through this process, (P=2, S=1) is set.

When the position number of the microlens array 121 is incremented, the processing circuitry 21 acquires the image data for the iPS cells by the imaging control function 211 (step S46). When the image data is acquired, the processing circuitry 21 performs predetermined image processing on the acquired image data via the image processing function 214 to generate an image. The processing circuitry 21 stores the generated image in the memory 22 (step S47).

When the image is stored in the memory 22, the processing circuitry 21 determines whether or not imaging is performed at all preset positions, by the imaging control function 211 (step S48). If the imaging is not performed at all the positions (No in step S48), the processing circuitry 21 transfers the process to step S44, and repeats the processes from step S44 to step S48 until imaging is performed at all the preset positions.

If the imaging is performed at all the preset positions (Yes in step S48), the processing circuitry 21 determines whether or not imaging of all preset iPS cells is performed, via the imaging control function 211 (step S49). If the imaging is not performed on all the iPS cells (No in step S49), the processing circuitry 21 causes the extendable part 1261 to extend or contract to return the microlens array 121 to an initial position (the first position), via the imaging control function 211 (step S410). When the microlens array 121 is returned to the initial position, the processing circuitry 21 sets the first position: P=1 (step S411). Through this process, (P=1, S=1) is set.

Subsequently, the processing circuitry 21 rotates the iPS cells accommodated in the wells (step S412). Specifically, the processing circuitry 21 executes, for example, the voltage control function 212. In the voltage control function 212, the processing circuitry 21 controls the power supply 30 to apply a voltage between the first electrode 111 and the second electrode 112 of the well plate 11. Thereby, electrostatic attraction is generated between the movable electrode plate 1111 provided in the first electrode 111 and the fixed electrode part 1121 provided in the second electrode 112, and the movable electrode plate 1111 rotates around the torsion bar 1113.

Figure 8:
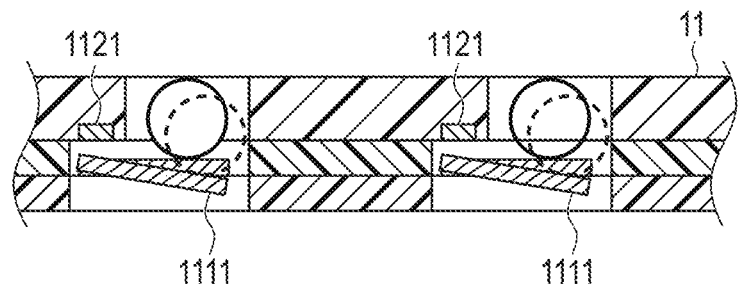
FIG. 8 is a diagram showing an example of a case where a movable electrode part shown in FIG. 2 rotates.

FIG. 8 is a schematic diagram showing an example of a case where the movable electrode plate 1111 rotates. According to FIG. 8, the movable electrode plate 1111 rotates so that a portion functioning as a bottom portion of the well is inclined in a vertically downward direction. Thereby, the iPS cell placed on the movable electrode plate 1111 rolls in the vertically downward direction.

The processing circuitry 21 may apply, for example, voltages a plurality of times, pulsewise, between the first electrode 111 and the second electrode 112. In addition, the processing circuitry 21 may apply a sine wave-formed voltage. Through application of voltages a plurality of times in the predetermined form between the first electrode 111 and the second electrode 112, the rotation and return of the movable electrode plate 1111 are repeated. Thereby, the iPS cell placed on the movable electrode plate 1111 is vibrated rotationally, and the probability that the iPS cell will rotate on the movable electrode plate 1111 is improved. The processing circuitry 21 applies a voltage between the first electrode 111 and the second electrode 112 so that, for example, the iPS cell rotates about a quarter of the way round.

Figure 9:
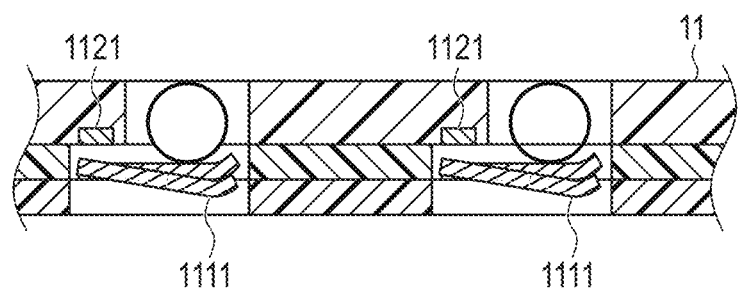
FIG. 9 is a diagram showing another example of the movable electrode part shown in FIG. 8.

A cross section of the movable electrode plate 1111 may have, for example, a shape along a vertically upward direction as shown in FIG. 9. By modifying the shape of the movable electrode plate 1111, it is possible to rotate the iPS cell more efficiently.

The processing circuitry 21 may also execute the water supply control function 213 when rotating the iPS cells. In the water supply control function 213, the processing circuitry 21 controls the pump to let the buffer solution flow into the imaging device 10 through the first hole 124. Thereby, flow of the buffer solution is generated in the imaging device 10, and a force in a direction from the first hole 124 to the second hole 125 acts on the iPS cells accommodated in the wells. This makes it possible to rotate the iPS cells more efficiently.

When all iPS cells accommodated in the wells are rotated, for example, about a quarter of the way round, the processing circuitry 21 increments the set image number (step S413). Through this process, (P=1, S=2) is set.

When the image number of the iPS cells is incremented, the processing circuitry 21 acquires image data for the iPS cells via the imaging control function 211 (step S414). When the image data is acquired, the processing circuitry 21 performs predetermined image processing on the acquired image data by the image processing function 214 to generate an image. The processing circuitry 21 stores the generated image in the memory 22 (step S415).

When the image is stored in the memory 22, the processing circuitry 21 transfers the process to step S48, and repeats the processes from step S44 to step S48 until imaging is performed at all the preset positions. In addition, the processing circuitry 21 repeats the processes from step S44 to step S415 until imaging of all the preset iPS cells is performed.

If imaging of all the preset iPS cells is performed (Yes in step S49), i.e., if images for (P=1, S=1), (P=2, S=1), . . . , (P=1, S=2), (P=2, S=2), . . . , and (P=Pn, S=Sm) are stored in the memory 22, the processing circuitry 21 executes the identification function 215. In the identification function 215, the processing circuitry 21 identifies iPS cells in a good state from among the iPS cells accommodated in the wells by using the learned model 221 stored in the memory 22 (step S416).

Figure 10:
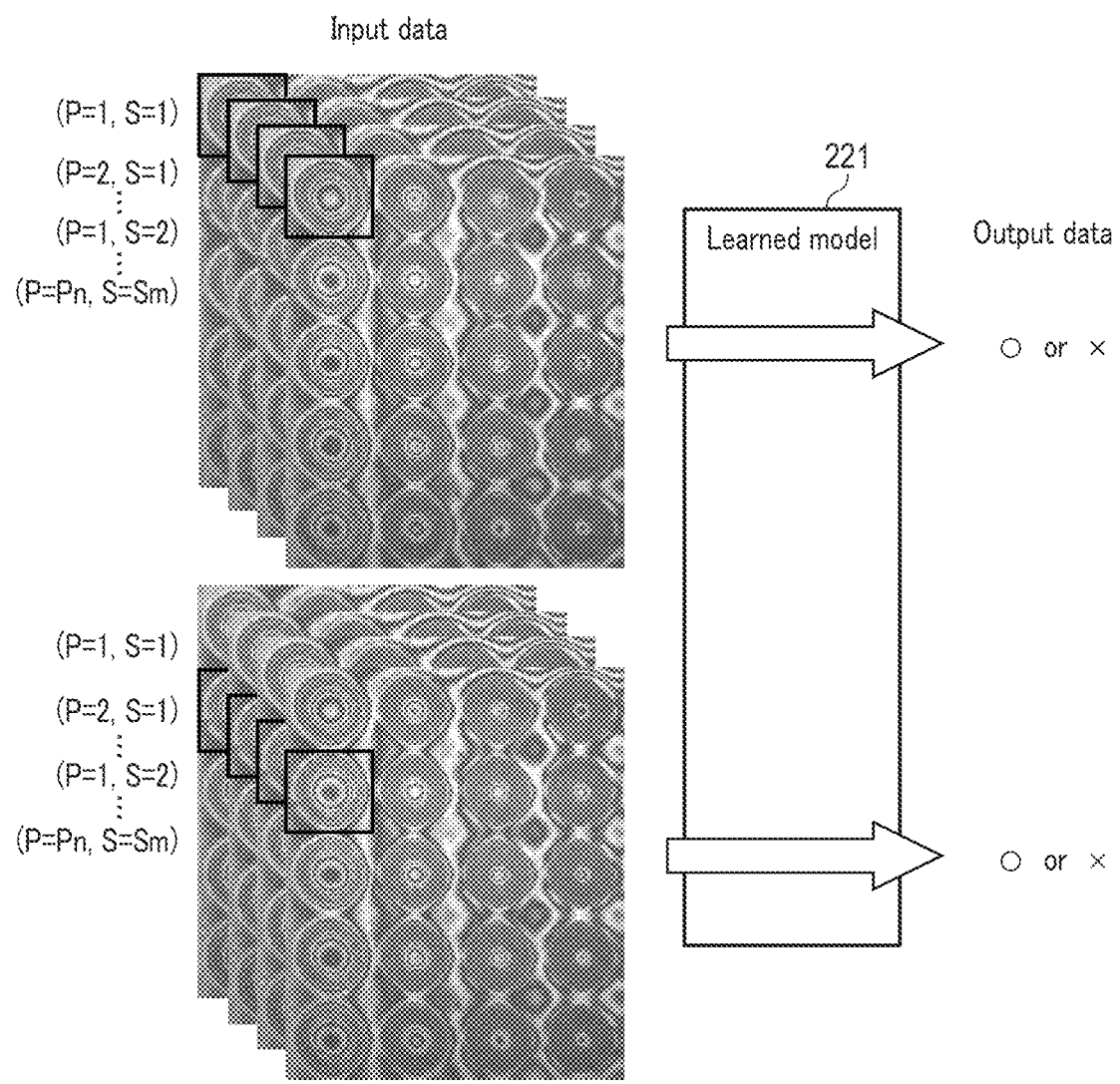
FIG. 10 is a diagram for explaining an operation of an identification function shown in FIG. 1.

FIG. 10 is a diagram for explaining an example of an operation of the identification function 215 shown in FIG. 1. The processing circuitry 21 reads, from the memory 22, respective images captured while changing a vertical position of the microlens array 121 relative to the well plate 11 and rotating the iPS cells. That is, the processing circuitry 21 reads the images for (P=1, S=1), (P=2, S=1), . . . , (P=1, S=2), (P=2, S=2), . . . , and (P=Pn, S=Sm) from the memory 22.

The processing circuitry 21 extracts a first iPS cell from each of the read images for (P=1, S=1), (P=2, S=1), . . . , (P=1, S=2), (P=2, S=2), . . . , and (P=Pn, S=Sm). According to FIG. 10, the first iPS cell is, for example, located at the uppermost row (a first row) and the leftmost column (a first column). The processing circuitry 21 inputs a plurality of images extracted for the first iPS cell to the learned model 221 as input data. From the learned model 221, information about a state of the first iPS cell, e.g., whether the state of the first iPS cell is good or bad, is output, based on the plurality of input images for the first iPS cell.

Subsequently, the processing circuitry 21 extracts a second iPS cell from each of the images for (P=1, S=1), (P=2, S=1), . . . , (P=1, S=2), (P=2, S=2), . . . , and (P=Pn, S=Sm). According to FIG. 10, the second iPS cell is, for example, located at a second row and the first column. The processing circuitry 21 inputs a plurality of images for the second iPS cell to the learned model 221 as input data. From the learned model 221, whether a state of the second iPS cell is good or bad is output, based on the plurality of input images for the second iPS cell.

The processing circuitry 21 inputs respective images for all the iPS cells included in the captured images to the learned model 221, and causes the learned model 221 to output the state of each iPS cell. When the states of all the iPS cells included in the captured images are output, the processing circuitry 21, for example, displays only iPS cells in a good state on the display 24.

If there is a well not accommodating an iPS cell, the processing circuitry 21 skips the well and extracts the iPS cell accommodated in the next well from the images.

The iPS cells identified as being in a good state are, for example, collected from the imaging device 10 and transferred to a culture dish by a predetermined number of cells. The iPS cells transferred to the culture dish form a colony, and are cultured as a cell colony in the culture dish.

In the above manner, in the first embodiment, the cell identification system includes the imaging device 10 and the identification device 20. The imaging device 10 includes the well plate 11, in which a plurality of wells capable of accommodating iPS cells are provided, the rotation mechanisms 111 and 112 configured to rotate the iPS cells accommodated in the wells, and the imaging parts 121 and 122 configured to image the iPS cells accommodated in the plurality of wells. Each time the iPS cells accommodated in the wells are rotated, the imaging device 10 images the iPS cells, and transmits an image signal to the identification device 20. The identification device 20 stores a learned model in advance. The identification device 20 inputs an image generated based on the image signal transmitted from the imaging device 10 to the learned model as input data, and identifies iPS cells in a good state based on the information to be output. Thereby, at the time of producing iPS cells and at an undifferentiated stage, it is possible to identify iPS cells in a good state without manual operation. Furthermore, even after the iPS cells are differentiated, it is possible to identify iPS cells in a good state without manual operation.

In addition, in the first embodiment, the imaging device 10 further includes the distance adjustment mechanism 1261 capable of adjusting a distance between the imaging parts 121 and 122 and the iPS cells accommodated in the wells. Each time the distance between the imaging parts 121 and 122 and the iPS cells accommodated in the wells is changed, the imaging device 10 images the iPS cells, and transmits an image signal to the identification device 20. Thereby, an image that can include an interference pattern of light will be acquired, and it is possible to acquire not only an appearance of an iPS cell but also images associated with the iPS cell's state of cytoplasm and nucleus states. By using the image including an interference pattern of light as input data, the precision of identifying iPS cells in a good state is improved.

In addition, in the first embodiment, the imaging part includes the microlens array 121 and the image sensor 122. Thereby, it is possible to generate an image including a plurality of iPS cells in a single action of imaging, and it is possible to pick up an image of a plurality of iPS cells efficiently.

In the explanation of the flowchart shown in FIG. 4, the processing beginning from the state in which the iPS cells are accommodated in the wells in the imaging device 10 is described. A method for efficiently trapping the iPS cells in the wells in the imaging device 10 can be realized in the following manner, for example.

Figure 11:
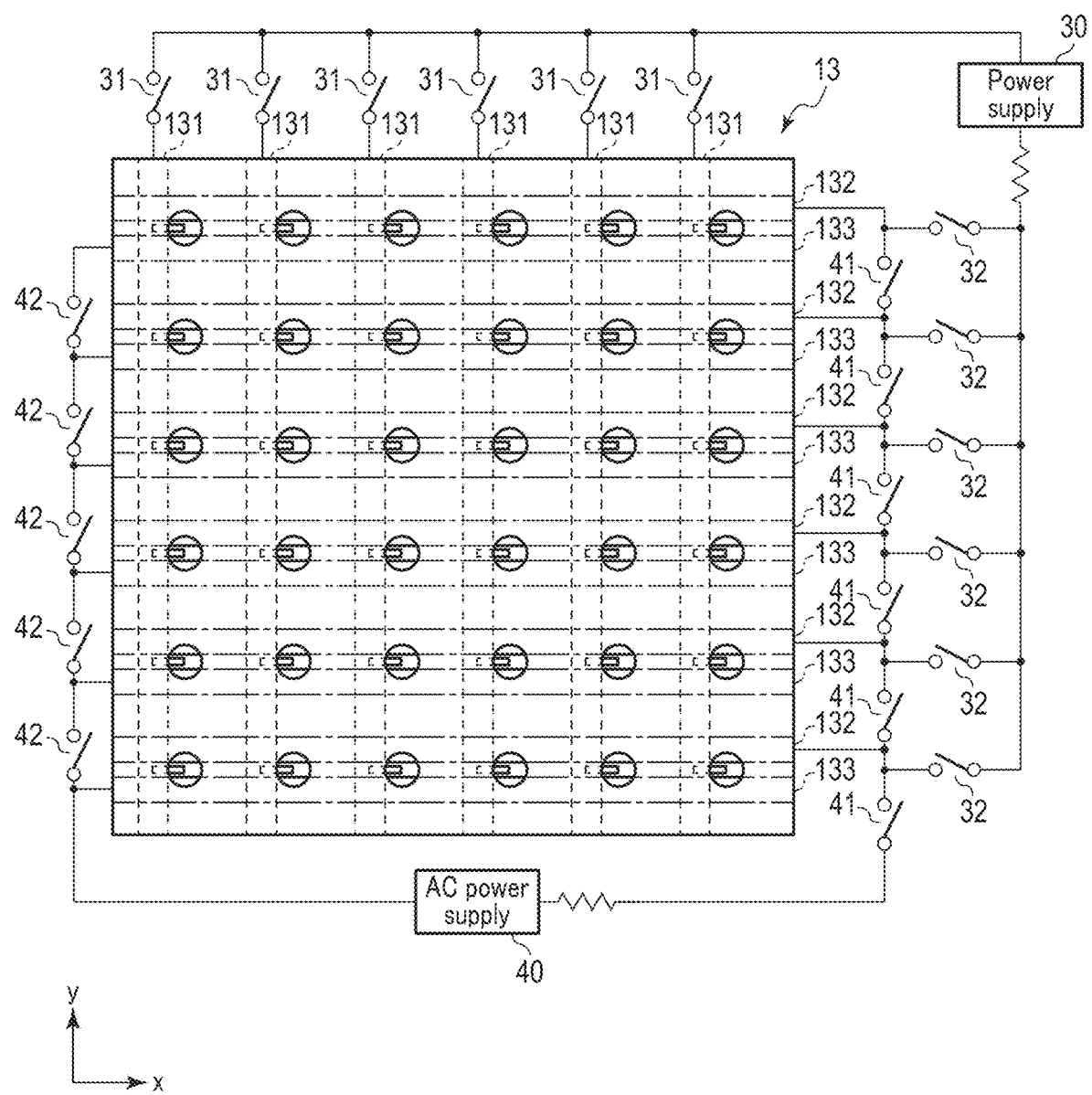
FIG. 11 is a diagram showing a top view of a well plate having a function of efficiently trapping iPS cells.

FIG. 11 is a diagram showing an example of a top view of a well plate 13 having a function of efficiently trapping iPS cells. Inside the well plate 13, trapping mechanisms that trap iPS cells in wells and rotation mechanisms that rotate the iPS cells trapped in the wells are formed. The trapping mechanisms and the rotation mechanisms are realized by, for example, third electrodes 131, fourth electrodes 132, and fifth electrodes 133, formed inside the well plate 13.

Specifically, the third electrodes 131, the fourth electrodes 132, and the fifth electrodes 133 are respectively formed in preset directions. For example, in the example shown in FIG. 11, the third electrodes 131 are indicated by broken lines, along a y-axis direction, and formed in the vicinity of one side surface of each well. The fourth electrodes 132 and the fifth electrodes 133 are indicated by one-dot chain lines, along an x-axis direction, and formed to sandwich the wells. A distance between the fourth electrode 132 and the fifth electrode 133 formed to sandwich the wells is shorter than the diameter of the well.

The third electrodes 131 and the fourth electrodes 132 are connected to the power supply 30 via switches 31 and switches 32, respectively, so as to generate a potential difference between the third electrodes 131 and the fourth electrodes 132. In addition, the fourth electrodes 132 and the fifth electrodes 133 are connected to an AC power supply 40 via switches 41 and switches 42, respectively, so as to generate a potential difference between the fourth electrodes 132 and the fifth electrodes 133.

Figure 12:
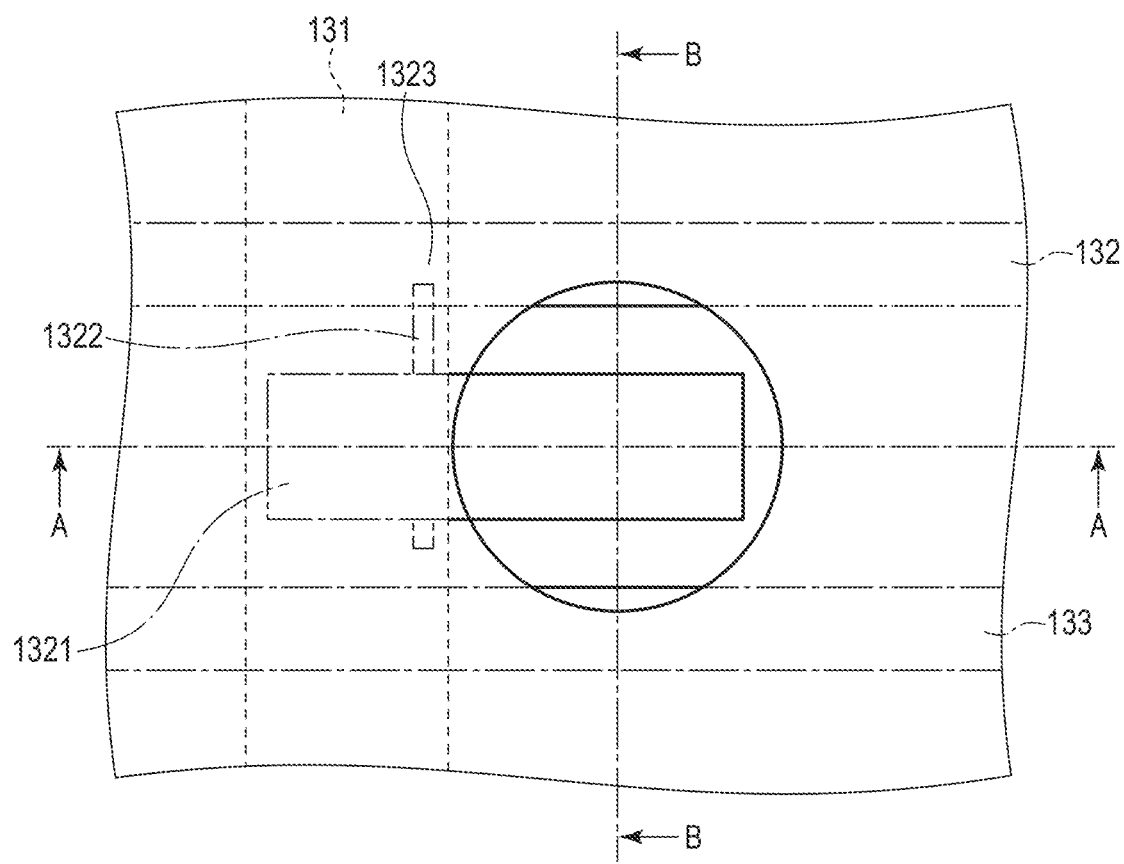
FIG. 12 is a diagram showing an enlarged configuration in the vicinity of a well of the well plate shown in FIG. 11.
Figure 13:
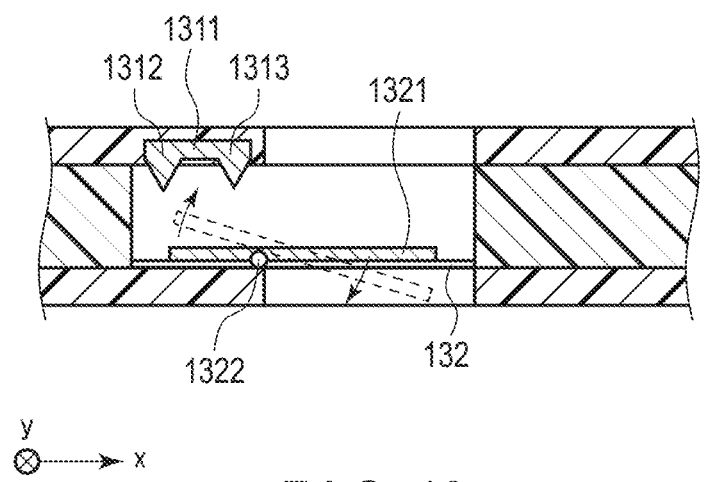
FIG. 13 is a cross-sectional diagram taken along a line A-A of the well plate shown in FIG. 12.
Figure 14:
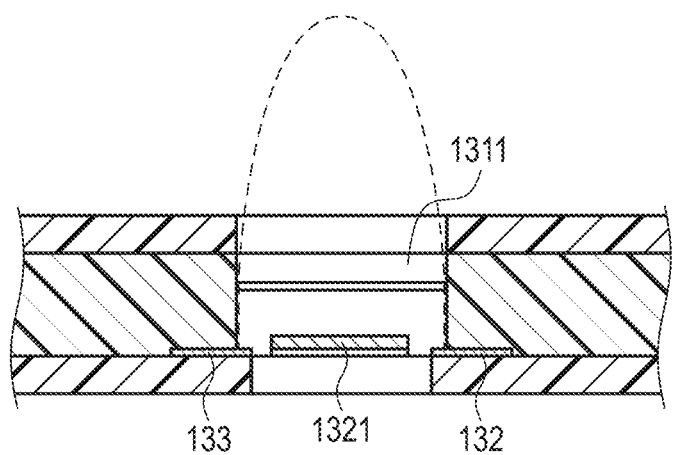
FIG. 14 is a cross-sectional diagram taken along a line B-B of the well plate shown in FIG. 12.

FIG. 12 is a diagram showing an enlarged configuration in the vicinity of a well of the well plate 13 shown in FIG. 11. FIG. 13 is a cross-sectional diagram taken along a line A-A of the well plate 13 shown in FIG. 12. FIG. 14 is a cross-sectional diagram taken along a line B-B of the well plate 13 shown in FIG. 12.

The third electrode 131 is disposed in an upper layer of the fourth electrode 132 and the fifth electrode 133. The third electrode 131 includes a driving electrode part 1311 at a vertically upper portion of an area sandwiched between the fourth electrode 132 and the fifth electrode 133. The driving electrode part 1311 is exposed to a space provided in the well plate 13. The driving electrode part 1311 is formed to include triangular prism parts 1312 and 1313 having a triangular cross section in an area exposed to the internal space. The triangular prism parts 1312 and 1313 are formed in parallel along the y-axis direction. The driving electrode part 1311 including the triangular prism parts 1312 and 1313 makes it possible to exert an electrostatic force effectively. The driving electrode part 1311 may not necessarily include the triangular prism parts 1312 and 1313.

The fourth electrode 132 includes a movable electrode plate 1321, a torsion bar 1322, and a fixing part 1323. The movable electrode plate 1321 is formed in each well so as to be a partition plate of the cylindrical structure inside the well. The movable electrode plate 1321 functions as a bottom portion of each well. The movable electrode plate 1321 is supported by the fixing part 1323 via the conductive torsion bar 1322. A periphery of the movable electrode plate 1321 is formed with a space so that the movable electrode plate 1321 is rotatable around the torsion bar 1322. By the movable electrode plate 1321, the torsion bar 1322, and the fixing part 1323, an electrostatic type rotation actuator as a rotation mechanism is formed in each well.

The fourth electrode 132 and the fifth electrode 133 function as a trapping mechanism. A distance between the fourth electrode 132 and the fifth electrode 133 formed to sandwich the well is shorter than the diameter of the well, and the fourth electrode 132 and the fifth electrode 133 are formed to protrude into the well. In a state in which the imaging device 10 is filled with a buffer solution, if an AC voltage is applied between the fourth electrode 132 and the fifth electrode 133 by the AC power supply, a dielectric migration force is generated in a direction toward an internal portion of the well as shown in FIG. 14.

By using the imaging device 10 including the well plate 13 shown in FIGS. 11-14, iPS cells are, for example, trapped by the wells in the imaging device 10 in the following manner. For example, isolated iPS cells are contained in a buffer solution, and introduced into the imaging device 10 from the first hole 124 together with the buffer solution.

Figure 15:
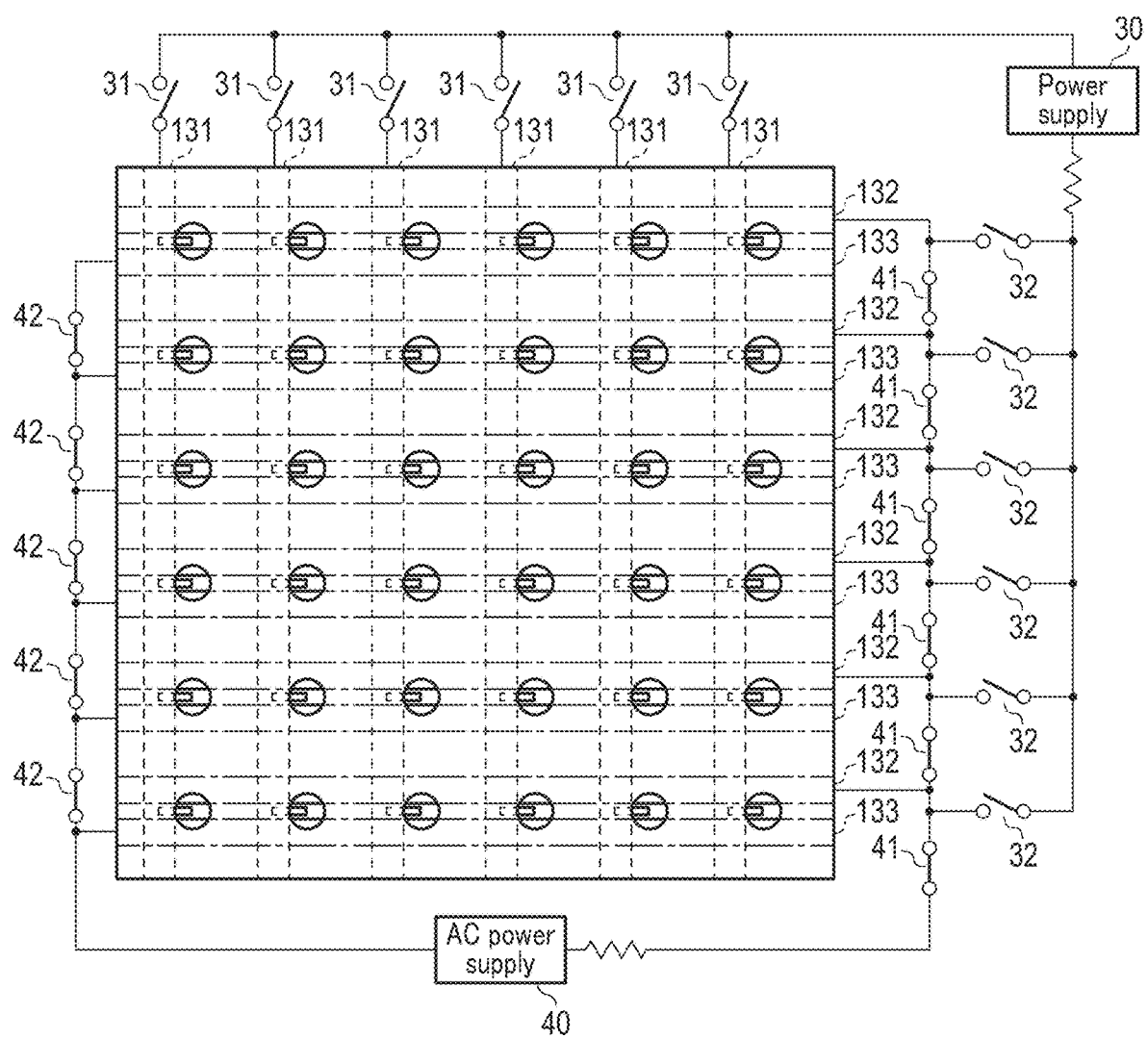
FIG. 15 is a diagram showing connections of switches when trapping the iPS cells by the wells of the well plate.
Figure 16:
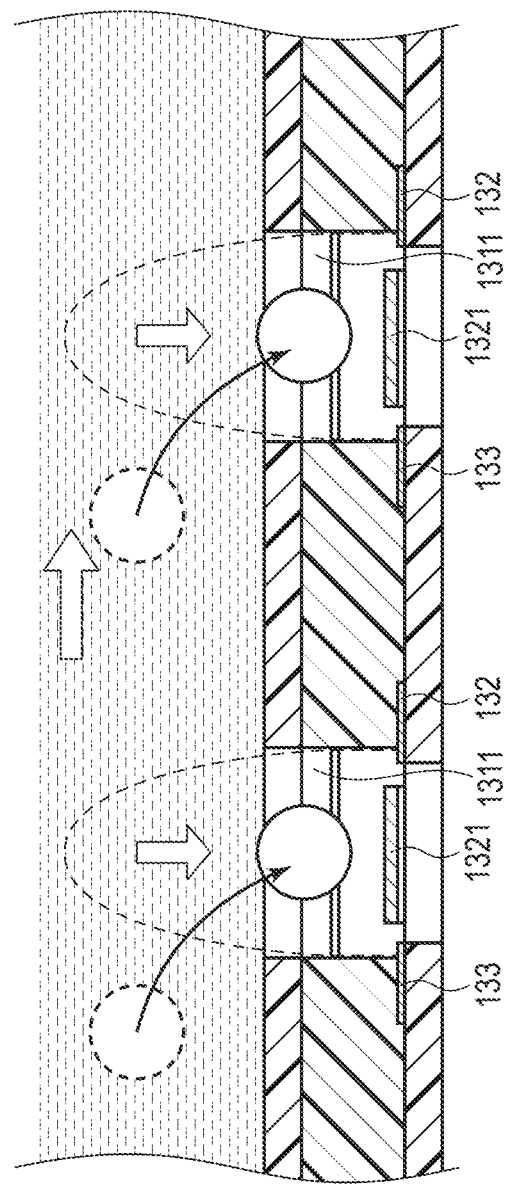
FIG. 16 is a cross-sectional diagram of the well plate having a function of efficiently trapping the iPS cells.

FIG. 15 is a diagram showing connection examples of the switches 31, 32, 41, and 42 when trapping the iPS cells by the wells of the well plate 13. When trapping the iPS cells by the wells of the well plate 13, the switches 31 and 32 are opened, and the switches 41 and 42 are closed so that an AC voltage is applied between the fourth electrodes 132 and the fifth electrodes 133. The buffer solution containing the iPS cells passes between the well plate 13 and the lid part 12 in the imaging device 10, and is then discharged from the second hole 125. When the buffer solution flows over the wells, the iPS cells contained in the buffer solution receive the dielectric migration force generated by the fourth electrodes 132 and the fifth electrodes 133 as shown in FIG. 16. Thereby, the iPS cells are trapped by the wells.

Figure 17:
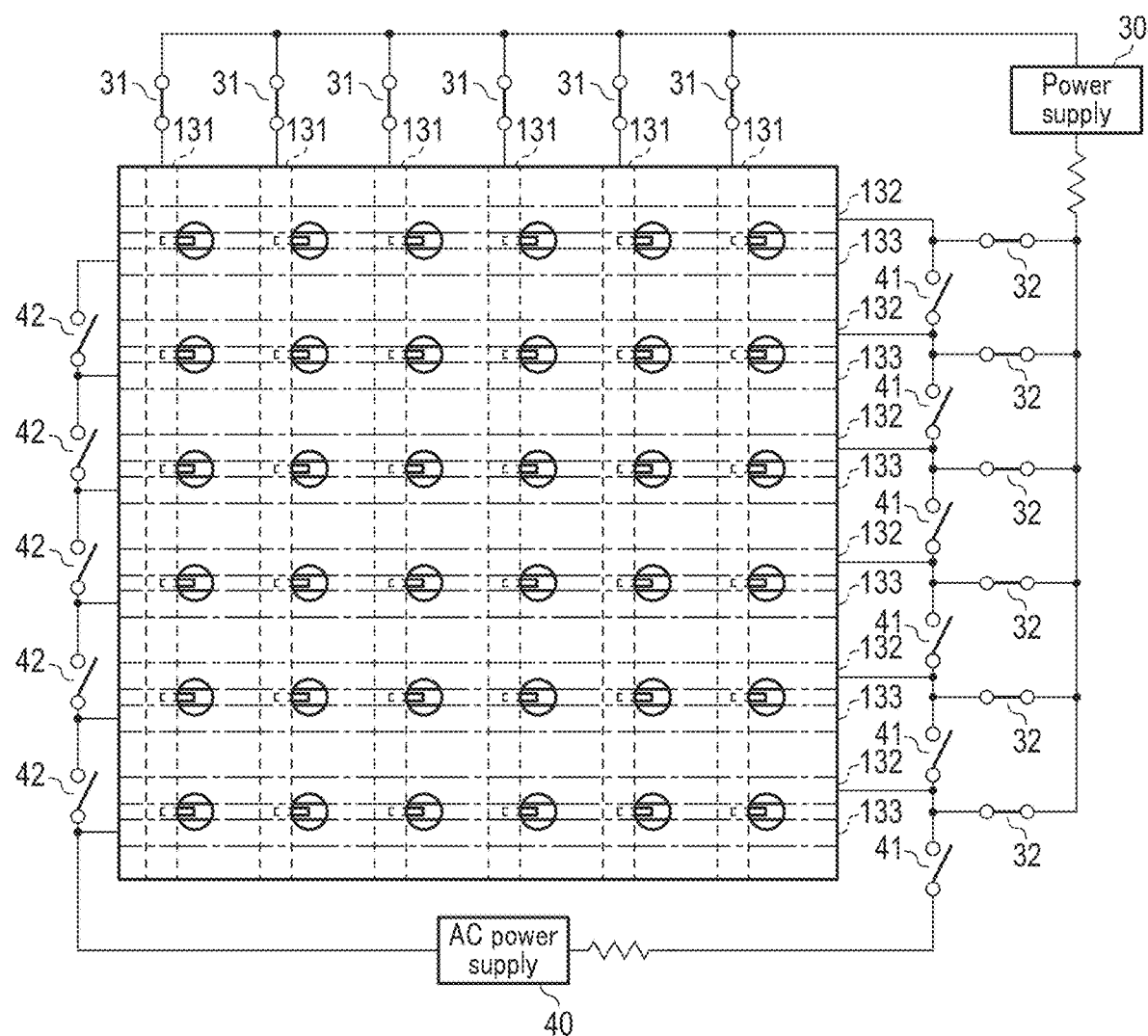
FIG. 17 is a diagram showing connections of switches when rotating the iPS cells trapped by the wells.

FIG. 17 is a diagram showing connection examples of the switches 31, 32, 41, and 42 when rotating the iPS cells trapped by the wells. When rotating the iPS cells trapped by the wells, the switches 31 and 32 are closed, and the switches 41 and 42 are opened so that a voltage is applied between the third electrodes 131 and the fourth electrodes 132.

The cells during culture to be introduced into the imaging device 10 may be iPS cells that have undergone the identification described in the first embodiment, identified as being in a good state, and are collected and cultured. Concentration and purification of the good iPS cells can thereby be performed.

Second Embodiment

In the first embodiment, an example of identifying whether or not the states of the iPS cells accommodated in the wells are good through use of the learned model 221 has been described. In a second embodiment, an example of identifying whether or not states of cell colonies accommodated in the wells are good through use of a learned model will be described.

Figure 18:
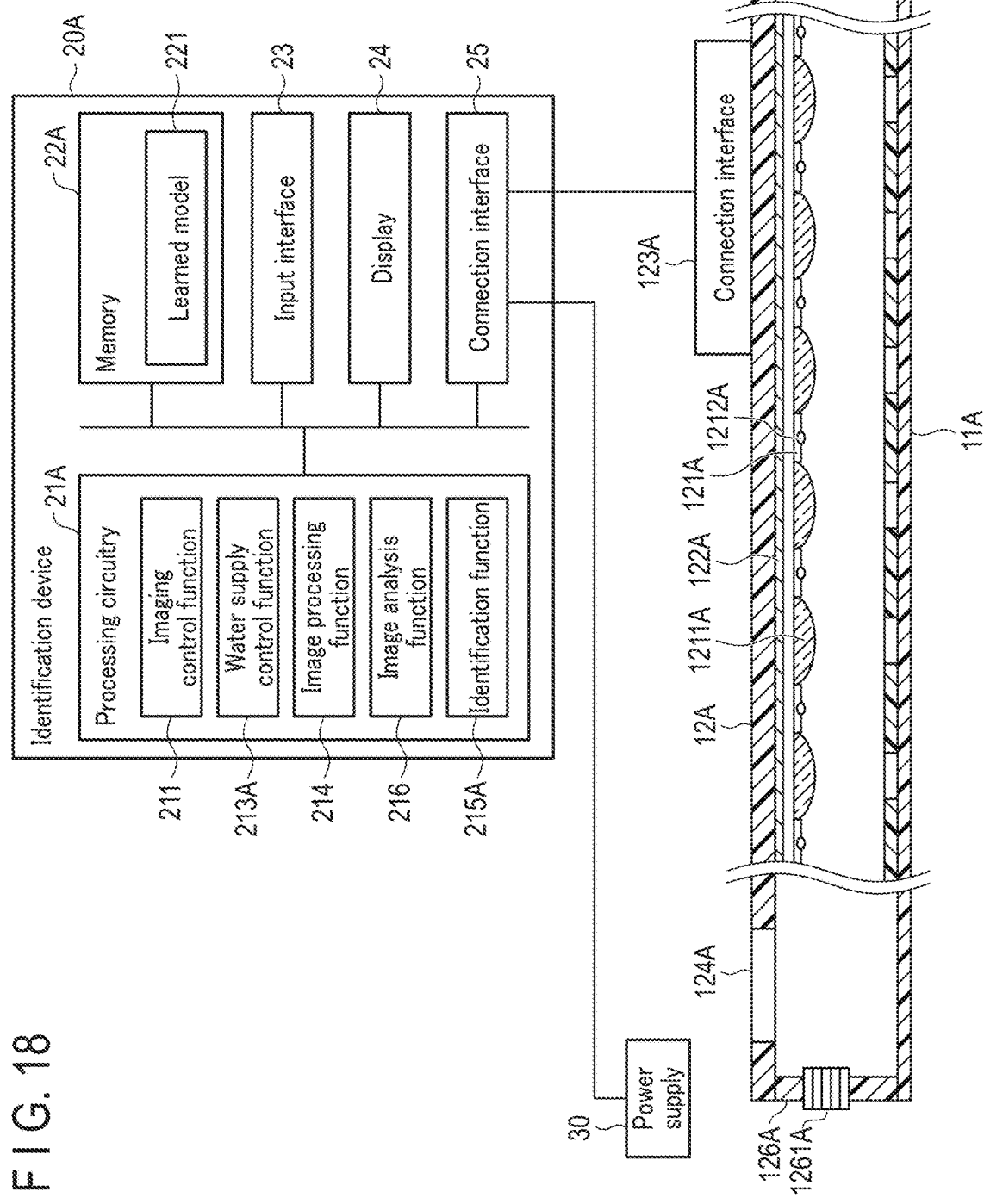
FIG. 18 is a diagram showing a configuration of a cell identification system according to a second embodiment.

FIG. 18 is a diagram showing an example of a configuration of a cell identification system according to the second embodiment. The cell identification system shown in FIG. 18 includes an imaging device 10A and an identification device 20A. FIG. 18 shows a schematic diagram of a cross section of the imaging device 10A and a block diagram of the identification device 20A. The imaging device 10A and the identification device 20A are, for example, wire-connected. In addition, the identification device 20A is connected to the power supply 30 that applies a voltage to the imaging device 10A.

The imaging device 10A is a device capable of accommodating cell colonies and imaging the accommodated cell colonies. The cell colonies to be accommodated in the imaging device 10A are preferably two-dimensional cell colonies in which iPS cells are two-dimensionally distributed. The distribution of the iPS cells is not necessarily limited to be two-dimensional. The imaging device 10A includes a well plate 11A for accommodating the cell colonies, and a lid part 12A that covers the well plate 11A tightly.

The well plate 11A is made of, for example, a thermoplastic resin, such as PDMS, polyethylene, and polystyrene, that has flexibility. In the well plate 11A, a plurality of recesses called "wells" are formed, for example, in a lattice pattern on its top surface. In other words, a well array is formed on the well plate 11A. Each well is formed into a cylindrical shape having an approximately circular cross section. A diameter of the well is about a few millimeters, and capable of accommodating a cell colony.

The lid part 12A is made of, for example, a silicon such as PDMS or a resin such as ABS. At a part of an upper internal surface of the lid part 12A, an imaging part for imaging the cell colonies accommodated in the wells of the well plate 11A is provided. The imaging part includes, for example, a plurality of lens elements 1211A and an image sensor 122A. In the following, a plurality of wells are formed in a lattice pattern on the well plate 11A, assuming a microlens array 121A formed of the plurality of lens elements 1211A arranged in a lattice pattern in the same manner as the wells. The arrangement of the lens elements 1211A in the microlens array 121A is matched with that of the wells formed in the well plate 11A.

Light sources 1212A are provided in the microlens array 121A. Each of the light sources 1212A is realized by, for example, a white LED, or an LED having a specific wavelength, etc. Each of the light sources 1212A is provided, for example, between adjacent lens elements 1211A as shown in FIG. 18. The light sources 1212A may be provided on the rear side of the well plate 11A. From the light sources 1212A, light having energy of a degree not liable to damage the cell colonies accommodated in the wells is emitted.

The image sensor 122A is an example of an image sensor that converts received light to an electric signal. The image sensor 122 is realized by, for example, a CCD sensor or a CMOS sensor. The image sensor 122A receives light emitted from the light sources 1212A and reflected and scattered by an imaging object through the microlens array 121A. In a case where the light sources 1212A are provided on the rear side of the well plate 11A, the image sensor 122A receives light that passes through the well plate 11A and the imaging object through the microlens array 121A. The image sensor 122A converts the received light into an image signal as an electric signal.

On an upper external surface of the lid part 12A, for example, a connection interface 123A for connecting the imaging part and the identification device 20A is provided. On an upper surface of an area where the imaging part is not provided at an end of the lid part 12A, a first hole 124A is provided. In addition, on an upper surface of an area where the imaging part is not provided at the other end of the lid part 12A, a second hole 125A is provided. The first hole 124A is used as, for example, an inflow port that allows a solution such as a buffer solution to flow into the imaging device 10. In addition, the second hole 125A is used as, for example, a discharge port that discharges a solution such as a buffer solution from the imaging device 10.

The lid part 12A includes a side wall part 126A. On at least a part of the side wall part 126A, for example, an extendable part 1261A capable of extending and contracting in an extending direction of the side wall part 126A is formed. The extendable part 1261A is an example of a distance adjustment mechanism. The extendable part 1261A is realized by, for example, a bellows structure, a nesting structure, etc. Through the extension and contraction of the extendable part 1261A, a distance between the top surface of the well plate 11A and the microlens array 121A changes.

The identification device 20A shown in FIG. 18 is a device that identifies cell colonies in a good state from among the cell colonies accommodated in the imaging device 10A through use of the learned model. The identification device 20A includes processing circuitry 21A, a memory 22A, the input interface 23, the display 24, and the connection interface 25. The processing circuitry 21A, the memory 22A, the input interface 23, the display 24, and the connection interface 25 are, for example, connected in a communicable fashion to one another via a bus.

The processing circuitry 21A is a processor functioning as a main device of the identification device 20A. The processing circuitry 21A executes a program stored in the memory 22A, etc. so as to realize a function corresponding to the program.

The memory 22A is a storage device that stores various kinds of information. The memory 22A stores an identification program, etc. according to the present embodiment. The memory 22A also stores, for example, the learned model 221 as an identifier generated by machine learning.

The processing circuitry 21A executes the identification program, etc. stored in the memory 22A so as to realize a function corresponding to the program. For example, through execution of the identification program, the processing circuitry 21A performs the imaging control function 211, a water supply control function 213A, the image processing function 214, an image analysis function 216, and an identification function 215A. In the present embodiment, a case where the imaging control function 211, the water supply control function 213A, the image processing function 214, the image analysis function 216, and the identification function 215A are realized by a single processor is described; however, the present invention is not limited thereto. For example, a plurality of independent processors may be combined to form processing circuitry, so that each of the processors executes a program to thereby realize the imaging control function 211, the water supply control function 213A, the image processing function 214, the image analysis function 216, and the identification function 215A.

The water supply control function 213A is a function to control a pump (not shown) to thereby supply a solution such as a buffer solution into the imaging device 10A.

The image analysis function 216 is a function to analyze a generated image. In the image analysis function 216, the processing circuitry 21A, for example, performs predetermined outline extraction processing on the generated image to extract areas including iPS cells from an image obtained through the imaging of a cell colony.

The identification function 215A is a function to identify cell colonies in a good state by using the learned model 221 with the image generated by the image analysis as an input.

Next, identification processing of the cell colonies by the identification device 20A configured as described above will be described in accordance with a processing procedure of the processing circuitry 21A.

Figure 19:
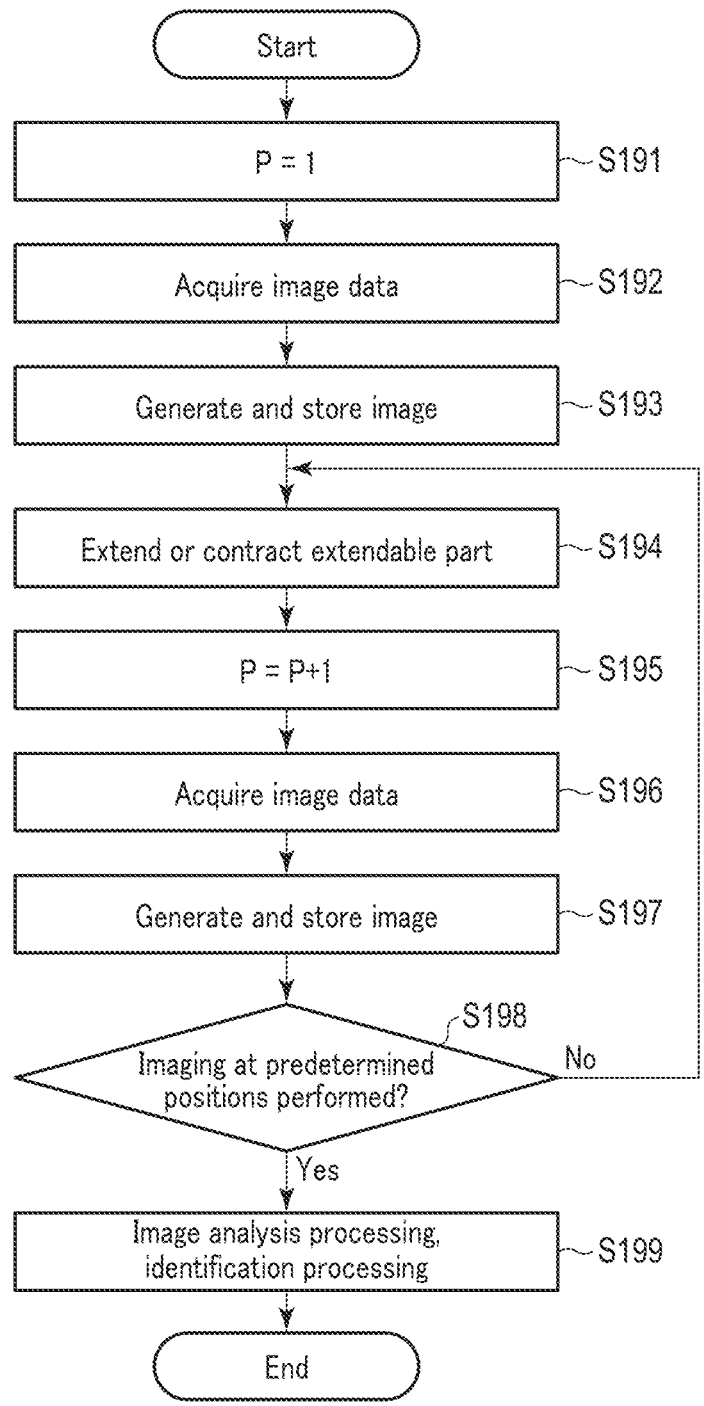
FIG. 19 is a flowchart showing operations when processing circuitry shown in FIG. 18 executes identification processing.

FIG. 19 is a flowchart showing an example of operations performed when the processing circuitry 21A shown in FIG. 18 executes identification processing of the cell colonies using the learned model 221.

First, an operator prepares the imaging device 10A. Specifically, the operator places cell colonies in the wells formed in the well plate 11A. After placing the cell colonies in the wells, the operator aligns the position of the wells formed in the well plate 11A and that of the microlens array 121A provided in the lid part 12A, and covers and fixes the well plate 11A with the lid part 12A.

Figure 20:
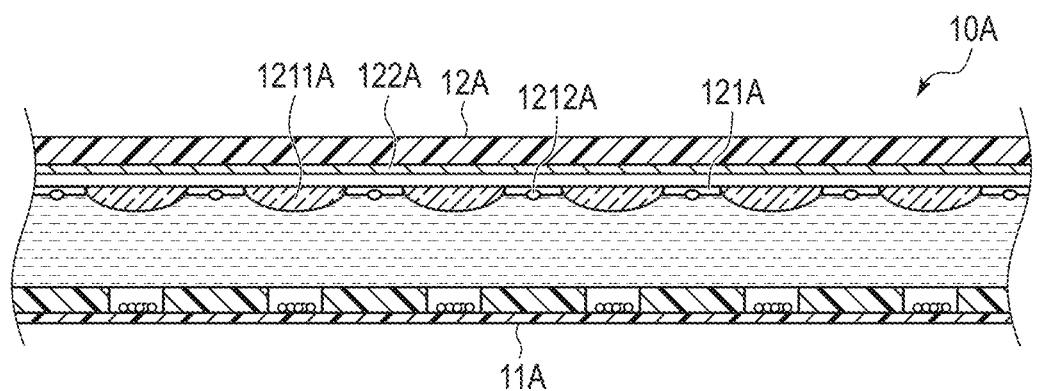
FIG. 20 is a cross-sectional diagram of an imaging device accommodating iPS cells and filled with a buffer solution.

After covering and fixing the well plate 11A with the lid part 12A, the operator causes the processing circuitry 21A to execute the water supply control function 213A via the input interface 23. When the water supply control function 213A is executed, the processing circuitry 21A controls the pump, for example, to supply the buffer solution to the imaging device 10A through the first hole 124A. Thereby, the imaging device 10A is filled with, for example, the buffer solution. FIG. 20 is a diagram showing an example of a cross section of the imaging device 10A accommodating the cell colonies and filled with the buffer solution.

When preparation of the imaging device 10A is completed, the operator inputs an instruction to start identification processing to the identification device 20A via the input interface 23. When the start instruction is input, the processing circuitry 21A reads an identification program from the memory 22A, and executes the read identification program. When the processing circuitry 21A executes the identification program, processing shown in FIG. 19 is started.

In FIG. 19, the processing circuitry 21A executes the imaging control function 211. When the imaging control function 211 is executed, the processing circuitry 21A sets the first position: P=1 of the microlens array 121A with respect to the well plate 11A (step S191). When the first position: P=1 is set, the processing circuitry 21A acquires image data based on an image signal about a cell colony obtained by the imaging device 10A (step S192).

When the image data is acquired, the processing circuitry 21A executes the image processing function 214. When the image processing function 214 is executed, the processing circuitry 21A performs predetermined image processing on the received image data to generate an image. The processing circuitry 21A stores the generated image in the memory 22A (step S193).

When the image is stored in the memory 22A, the processing circuitry 21A causes the extendable part 1261A, which is a distance adjustment mechanism, to extend or contract by the imaging control function 211 (step S194). Through this process, the microlens array 121A is moved to a second position: P=2. When the extendable part 1261A is caused to extend or contract, the processing circuitry 21A increments the set position number (step S195). Through this process, the second position: P=2 is set.

When the position number of the microlens array 121A is incremented, the processing circuitry 21A acquires image data for the cell colony by the imaging control function 211 (step S196). When the image data is acquired, the processing circuitry 21A performs predetermined image processing on the acquired image data by the image processing function 214 to generate an image. The processing circuitry 21A stores the generated image in the memory 22A (step S197).

When the image is stored in the memory 22A, the processing circuitry 21A determines whether or not imaging is performed at all preset positions, by the imaging control function 211 (step S198). If the imaging is not performed at all the positions (No in step S198), the processing circuitry 21A transfers the process to step S194, and repeats the processes from step S194 to step S198 until imaging is performed at all the preset positions.

If imaging is performed at all the preset positions (Yes in step S198), i.e., if images for the first position: P=1, the second position: P=2, . . . , the nth position: P=Pn are stored in the memory 22A, the processing circuitry 21A executes the image analysis function 216 and the identification function 215A (step S199).

Specifically, when the image analysis function 216 and the identification function 215A are executed, the processing circuitry 21A reads the images for the first position: P=1, the second position: P=2, . . . , the nth position: P=Pn from the memory 22A. The processing circuitry 21A extracts a first cell colony from each of the plurality of read images. As an example, in the generated images, the first cell colony is, for example, located at the uppermost row (a first row) and the leftmost column (a first column) as in the case of FIG. 10.

Figure 21:
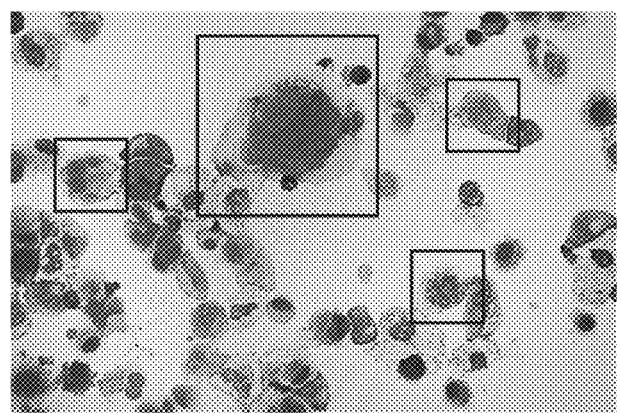
FIG. 21 is a diagram showing image analysis processing by an image analysis function shown in FIG. 18.

The processing circuitry 21A performs predetermined outline extraction processing on the images for the extracted first cell colony so as to extract areas in which iPS cells are included. FIG. 21 is a schematic diagram showing an example of image analysis processing by the image analysis function 216 shown in FIG. 18. According to FIG. 21, a plurality of areas in which iPS cells are included are extracted from an image for a cell colony.

The processing circuitry 21A performs the outline extraction processing for the multiple images from which the first cell colony is extracted so as to extract a plurality of areas in which iPS cells are included. At this time, there is an image in which the outline of an iPS cell is unclear depending on a positional relationship between the well plate 11A and the microlens array 121A. In such an image, the processing circuitry 21A may use a position of the iPS cell extracted in another image among the multiple images, so as to extract an area in which the iPS cell is included.

Figure 22:
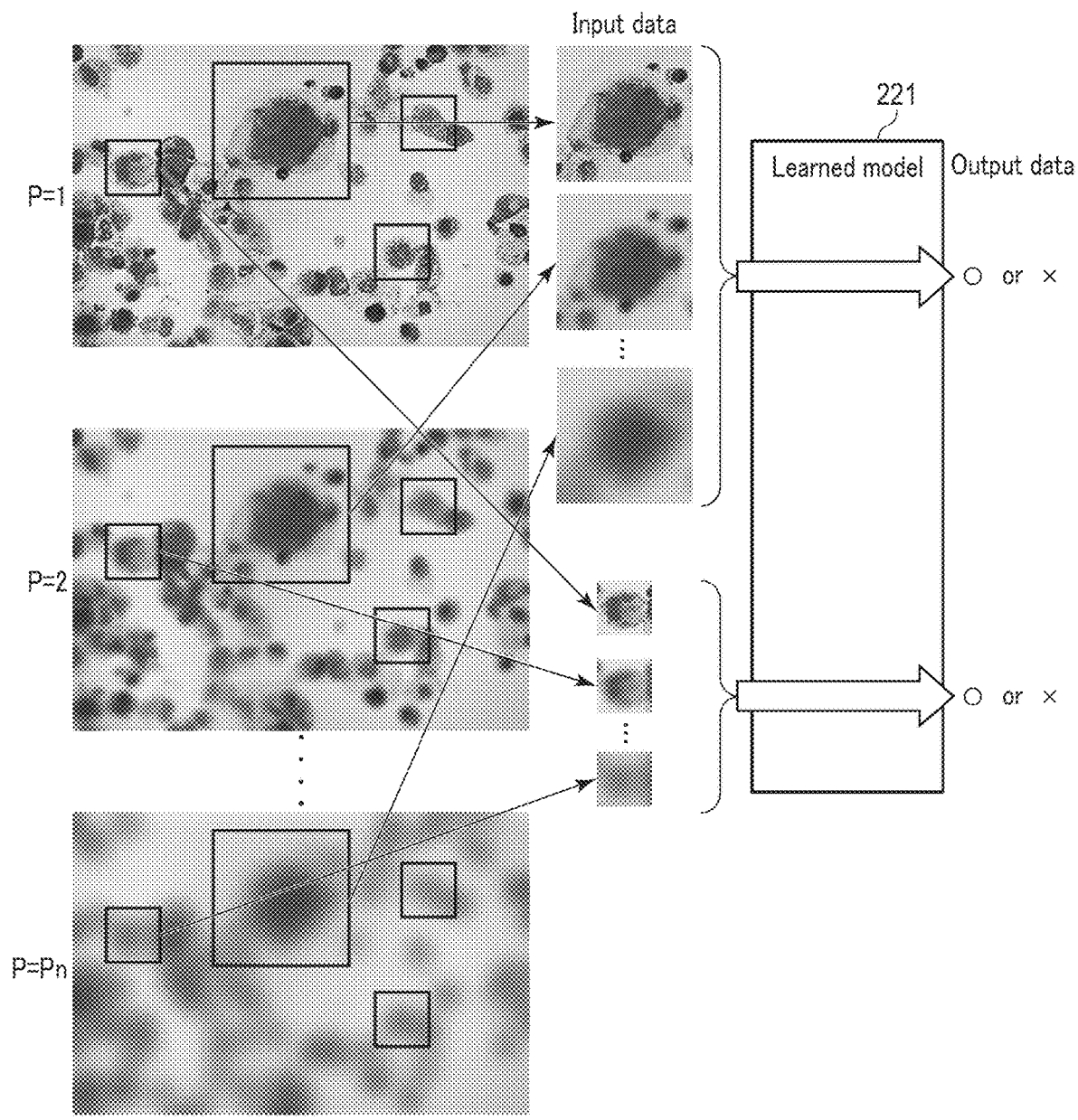
FIG. 22 is a diagram for explaining an operation of an identification function shown in FIG. 18.

FIG. 22 is a diagram for explaining an example of an operation of the identification function 215A shown in FIG.

18. The processing circuitry 21A extracts areas in which the iPS cells are included from each of the images for the first cell colony in the first position: P=1, the second position: P=2, . . . , the nth position: P=Pn. The processing circuitry 21A inputs a plurality of images extracted for the iPS cells to the learned model 221 as input data. From the learned model 221, whether the states of the iPS cells are good or bad is output, based on the plurality of input images for the iPS cells.

The processing circuitry 21A determines whether or not the state of the first cell colony is good based on the states of the iPS cells. For example, the processing circuitry 21A determines that the state of the first cell colony is good when the number of outputs indicating that the state is good is equal to or greater than a preset number. On the other hand, the processing circuitry 21A determines that the state of the first cell colony is bad when the number of outputs indicating that the state is good is less than the preset number.

Subsequently, the processing circuitry 21A extracts a second cell colony from each of the images for the first position: P=1, the second position: P=2, . . . , the nth position: P=Pn. The processing circuitry 21A repeats the same processing as that for the first cell colony to determine whether the state of the second cell colony is good or bad.

The processing circuitry 21A determines whether the state is good or bad for each of all the cell colonies included in the captured images. When the states of all the cell colonies included in the captured images are determined, the processing circuitry 21A displays, for example, only cell colonies in a good state on the display 24.

A cell colony identified as being in a good state is, for example, collected from the imaging device 10A, transferred to a culture dish, and cultured. Then, the cell colony cultured in the culture dish may be transferred again to the imaging device 10A, and its state determined as either is good or bad.

In the above manner, in the second embodiment, the cell identification system includes the imaging device 10A and the identification device 20A. The imaging device 10A includes the well plate 11A, in which a plurality of wells capable of accommodating cell colonies are provided; the imaging parts 121A and 122A configured to image the cell colonies accommodated in the plurality of wells; and the distance adjustment mechanism 1261A capable of adjusting a distance between the imaging parts 121A and 122A and the cell colonies accommodated in the wells. Each time the distance between the imaging parts 121A and 122A and the cell colonies accommodated in the wells is changed, the imaging device 10A images the cell colonies, and transmits an image signal to the identification device 20A. The identification device 20A stores the learned model in advance. The identification device 20A extracts areas including the iPS cells from an image generated based on the image signal transmitted from the imaging device 10A. The identification device 20A inputs the image including the iPS cells to the learned model as input data, and identifies cell colonies in a good state based on information to be output. Thereby, an image that can include an interference pattern of light will be acquired, and it is possible to acquire not only an appearance of an iPS cell but also images associated with a state in cytoplasm and a state of nucleus of the iPS cell. In addition, at the time of producing iPS cells and at an undifferentiated stage, it is possible to identify cell colonies in a good state without manual operation. Furthermore, even after the iPS cells are differentiated, it is possible to identify iPS cells in a good state without manual operation.

In the second embodiment, the imaging part includes the microlens array 121A and the image sensor 122A. Thereby, it is possible to generate an image including a plurality of cell colonies in a single action of imaging, and it is possible to image a plurality of cell colonies efficiently.

In the present embodiment, a case where the learned model 221 is generated by using images capturing iPS cells from multiple angles by changing the rotation direction and images captured while changing a distance between the iPS cells and the lens as input data is described. However, the present invention is not limited thereto. The learned model according to the present embodiment may be generated by using only the images captured while changing the distance between the iPS cells and the lens as the input data. That is, in the learned model according to the second embodiment, the images capturing the iPS cells from multiple angles need not necessarily be used as the input data.

In addition, in the first and second embodiments, a case where the light sources 1212 and 1212A provided in the imaging devices 10 and 10A are LEDs generating white light is described as an example. However, the present invention is not limited thereto. The light sources 1212 and 1212A may be laser light sources generating monochromatic light. In a case where the light sources 1212 and 1212A are realized by monochromatic laser light sources, it is possible to acquire a clear image if the iPS cells accommodated in the wells are stained by a fluorescent coloring matter to be excited by the monochromatic laser light sources.

In the first and second embodiments, an example of identifying whether the states of the iPS cells are good or bad by using the learned model 221 is described. However, the present invention is not limited thereto. An iPS cell that has reached an appropriate injection timing of a differentiation-inducing factor may be identified by using a learned model. At this time, the learned model is, for example, generated by machine learning with a plurality of images captured for iPS cells, which include an image for an iPS cell imaged at an appropriate injection timing of a differentiation-inducing factor, as input data, and whether or not the iPS cells in the images are at the appropriate timing for injecting a differentiation-inducing factor as correct answer output data. By inputting the images for the iPS cells obtained by imaging to this learned model, the processing circuitry of the identification device identifies an iPS cell that has reached the appropriate injection timing of a differentiation-inducing factor.

In addition, the identification processing of the iPS cells described in the first embodiment and the identification processing of the cell colonies described in the second embodiment may be performed in turn. That is, for example, a state of a cell colony, in which iPS cells identified as being in a good state through the identification described in the first embodiment are collected and cultured, may be identified by using the method described in the second embodiment. Furthermore, for example, an iPS cell may be isolated from cell colonies, in which the cell colonies identified as being in a good state through the identification described in the second embodiment are further cultured, and the state of this iPS cell may be identified by using the method described in the first embodiment.

According to at least one of the above-explained embodiments, the cell identification system can reduce a load of sorting the cells.

The term "processor" used in the descriptions of the embodiments refers to, for example, circuitry such as a central processing unit (CPU), a graphics processing unit (GPU), or an application-specific integrated circuit (ASIC), a programmable logic device (e.g., a simple programmable logic device (SPLD), a complex programmable logic device (CPLD), or a field programmable gate array (EPGA)), etc. The processor reads programs stored in the storage circuitry and executes them to realize the respective functions. The programs may be incorporated directly into circuitry of the processor, instead of being stored in the storage circuitry. In this case, the processor reads the programs incorporated into its circuitry and executes them to realize the respective functions. Each processor of the above embodiments is not necessarily configured as a single circuit, but may be configured by a combination of a plurality of independent circuits to realize their functions. Furthermore, a plurality of constituent elements in each of the above embodiments may be integrated into one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A cell identification system comprising:
an imaging device comprising:
   a well plate in which a plurality of wells capable of accommodating cells are provided;
   a rotation mechanism configured to rotate the cells accommodated in the wells; and
   an imaging part configured to image the cells accommodated in the wells; and
an identification device comprising processing circuitry configured to:
   control the rotation mechanism to rotate the cells accommodated in the wells;
   control the imaging part to image the cells accommodated in the wells each time the cells are rotated by the rotation mechanism; and
   input an image for the cells accommodated in the wells captured by the imaging part to a learned model so as to identify a cell in a good state from among the cells accommodated in the wells.

2. The cell identification system according to claim 1, wherein the imaging device further comprises a distance adjustment mechanism capable of adjusting a distance between the imaging part and the cells accommodated in the wells, and wherein the processing circuitry is further configured to control the imaging part to image the cells accommodated in the wells each time the distance is changed by the distance adjustment mechanism.

3. The cell identification system according to claim 1, wherein the imaging part further comprises:
   a microlens array including a plurality of lens elements arranged to correspond to positions at which the wells are formed; and
   an image sensor that converts light passing through the microlens array into an electric signal.

4. The cell identification system according to claim 1, wherein the rotation mechanism rotates the cells accommodated in the wells by vibrating the cells from a bottom portion of each of the wells.

5. The cell identification system according to claim 1, wherein the imaging device further comprises a trapping mechanism for trapping the cells in the wells.

6. A cell identification system comprising:
an imaging device comprising:
   a well plate in which a plurality of wells capable of accommodating cells are provided;
   an imaging part configured to image the cells accommodated in the wells; and
   a distance adjustment mechanism capable of adjusting a distance between the imaging part and the cells accommodated in the wells; and
an identification device comprising processing circuitry configured to:
   control the imaging part to image the cells accommodated in the wells each time the distance is changed by the distance adjustment mechanism; and
   input an image for the cells accommodated in the wells captured by the imaging part to a learned model so as to identify a cell in a good state from among the cells accommodated in the wells.

7. The cell identification system according to claim 6, wherein the imaging part further comprises:
   a microlens array including a plurality of lens elements arranged to correspond to positions at which the wells are formed; and
   an image sensor that converts light passing through the microlens array into an electric signal.

8. The cell identification system according to claim 6, wherein the imaging device further comprises a trapping mechanism for trapping the cells in the wells.

9. The cell identification system according to claim 6, wherein
   a cell colony of cells is accommodated in the well, and
   the imaging part images the cell colony accommodated in the well, wherein the processing circuitry is further configured to extract an image for the cells from an image for the cell colony accommodated in the well.

10. A cell identification system comprising:
an imaging device comprising:
   a well plate in which a plurality of wells capable of accommodating cells are provided; and
   an imaging part configured to image the cells accommodated in the wells; and
an identification device comprising processing circuitry configured to input an image for the cells accommodated in the wells captured by the imaging part to a learned model, so as to identify a cell in a good state from among the cells accommodated in the wells,
wherein the imaging part further comprises:
   a microlens array including a plurality of lens elements arranged to correspond to positions at which the wells are formed; and
   an image sensor that converts light passing through the microlens array into an electric signal.

11. The cell identification system according to claim 10, wherein the imaging device further comprises a trapping mechanism for trapping the cells in the wells.

12. The cell identification system according to claim 10, wherein
   a cell colony of cells is accommodated in the well, and
   the imaging part images the cell colony accommodated in the well, wherein the processing circuitry is further configured to extract an image for the cells from an image for the cell colony accommodated in the well.

13. A cell identification method comprising:
   imaging cells accommodated in a plurality of wells provided in an imaging device by an imaging part provided in the imaging device;

changing a distance between the imaging part and the cells by a distance adjustment mechanism provided in the imaging device;

imaging the cells by the imaging part after changing the distance;

rotating the cells by a rotation mechanism provided in the imaging device;

imaging the cells by the imaging part after rotating the cells;

changing the distance by the distance adjustment mechanism;

imaging the cells by the imaging part after changing the distance; and inputting a plurality of images for the cells obtained by the imaging to a learned model so as to identify a cell in a good state from among the cells.

* * * * *